US011229688B2

(12) United States Patent
Pilpel et al.

(10) Patent No.: US 11,229,688 B2
(45) Date of Patent: Jan. 25, 2022

(54) STABILIZED THROMBIN

(71) Applicant: Omrix Biopharmaceuticals Ltd., Rehovot (IL)

(72) Inventors: Yair Pilpel, Rehovot (IL); Sivan Doron, Moshav Arugot (IL); Yuri Zherdev, Rehovot (IL); Tamara Byk-Tennenbaum, Kiryat Ono (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 89 days.

(21) Appl. No.: 16/166,510

(22) Filed: Oct. 22, 2018

(65) Prior Publication Data

US 2019/0054156 A1   Feb. 21, 2019

Related U.S. Application Data

(62) Division of application No. 14/830,984, filed on Aug. 20, 2015, now Pat. No. 10,159,719.

(60) Provisional application No. 62/039,989, filed on Aug. 21, 2014.

(30) Foreign Application Priority Data

Aug. 21, 2014  (IL) .......................................... 234246

(51) Int. Cl.
| *A61K 38/48* | (2006.01) |
| *C12N 9/74* | (2006.01) |
| *C12N 15/115* | (2010.01) |
| *A61K 38/36* | (2006.01) |
| *A61K 47/26* | (2006.01) |
| *A61M 5/19* | (2006.01) |
| *C12N 15/113* | (2010.01) |
| *G01N 33/53* | (2006.01) |

(52) U.S. Cl.
CPC ........ *A61K 38/4833* (2013.01); *A61K 38/363* (2013.01); *A61K 47/26* (2013.01); *A61M 5/19* (2013.01); *C12N 9/6429* (2013.01); *C12N 15/113* (2013.01); *C12N 15/115* (2013.01); *C12Y 304/21005* (2013.01); *G01N 33/5308* (2013.01); *C12N 2310/113* (2013.01); *G01N 2333/974* (2013.01)

(58) Field of Classification Search
None
See application file for complete search history.

(56) References Cited

U.S. PATENT DOCUMENTS

| 4,409,334 | A | 10/1983 | Lill et al. |
| 5,218,088 | A | 6/1993 | Gorenstein et al. |
| 5,882,870 | A * | 3/1999 | Nadeau ................. C12N 15/115 435/13 |
| 6,001,311 | A | 12/1999 | Brennan |
| 6,423,493 | B1 | 7/2002 | Gorenstein et al. |
| 6,693,187 | B1 | 2/2004 | Dellinger |
| 7,067,641 | B2 | 6/2006 | Dellinger |
| 7,125,569 | B2 | 10/2006 | Nur et al. |
| 7,214,786 | B2 * | 5/2007 | Kovalic ................. A01G 22/00 536/23.6 |
| 7,351,561 | B2 | 4/2008 | Metzner et al. |
| 7,641,918 | B2 | 1/2010 | Nur et al. |
| 7,834,146 | B2 * | 11/2010 | Kovalic ................. C07H 21/04 435/419 |
| 8,063,018 | B2 | 11/2011 | Ni et al. |
| 8,394,372 | B2 | 3/2013 | Andersson et al. |
| 2008/0311104 | A1 | 12/2008 | Senderoff et al. |
| 2017/0321161 | A1 * | 11/2017 | Lant ..................... C11D 3/0094 |

FOREIGN PATENT DOCUMENTS

| AU | 2012244176 A1 | 11/2012 |
| EP | 0277096 | 7/1992 |
| EP | 0478827 | 4/1994 |
| EP | 1390485 | 10/2006 |
| WO | WO 1993/005822 | 4/1993 |
| WO | WO 1997/042897 | 11/1997 |
| WO | WO 1997/046202 | 12/1997 |
| WO | WO 1998/039352 | 9/1998 |
| WO | WO 1999/014226 | 3/1999 |
| WO | WO 1999/054459 | 10/1999 |
| WO | WO 2000/047599 | 8/2000 |
| WO | WO 2002/095019 | 11/2002 |
| WO | 03002592 A1 | 1/2003 |
| WO | WO 2007/025049 | 3/2007 |
| WO | WO 2008/157304 | 12/2008 |
| WO | WO 2010/033167 | 3/2010 |

OTHER PUBLICATIONS

Long et al. (RNA, 2008, vol. 14, pp. 2504-2512).*
Allart, B. et al., '1, 5-Anhydro-2-Deoxy-D-Altritol Oligonucleotides as Conformationally Restricted Analogues of RNA' Nucleosides & Nucleotides (1998) 17 pp. 1523-1526.
Bock, L. et al., 'Selection of single-stranded DNA molecules that bind and inhibit human thrombin.' Nature (1992) 355 pp. 564-566.
Brennan, T. et al., 'Two-Dimensional Parallel Array Technology as a New Approach to Automated Combinatorial Solid-Phase Organic Synthesis' (1998) Biotechnol Bioeng., 61 (1) pp. 33-45.
Caruthers, M.H. et al, 'Chemical Synthesis of Deoxyoligonucleotides and Deoxyoligonucleotide Analogs' Methods in Enzymology (1992) 211 pp. 3-20.
Chang, J.Y., 'The structures and proteolytic specificities of autolysed human thrombin' Biochem. J. (1986) 240:797-802.
DeAnda, Jr., A. et al., 'Pilot Study of the Efficacy of a Thrombin Inhibitor for Use During Cardiopulmonary Bypass' Ann Thorac Surg. (1994) 58(2) pp. 344-350.

(Continued)

*Primary Examiner* — Hope A Robinson
(74) *Attorney, Agent, or Firm* — David R. Crichton

(57) ABSTRACT

The present invention is directed to compounds, methods for stabilizing thrombin activity with a thrombin binding oligonucleotide and to stabilized thrombin. The thrombin binding oligonucleotide is capable of inhibiting thrombin activity whereby the inhibition can be reversed with an antisense oligonucleotide.

6 Claims, 9 Drawing Sheets

Figure 1:
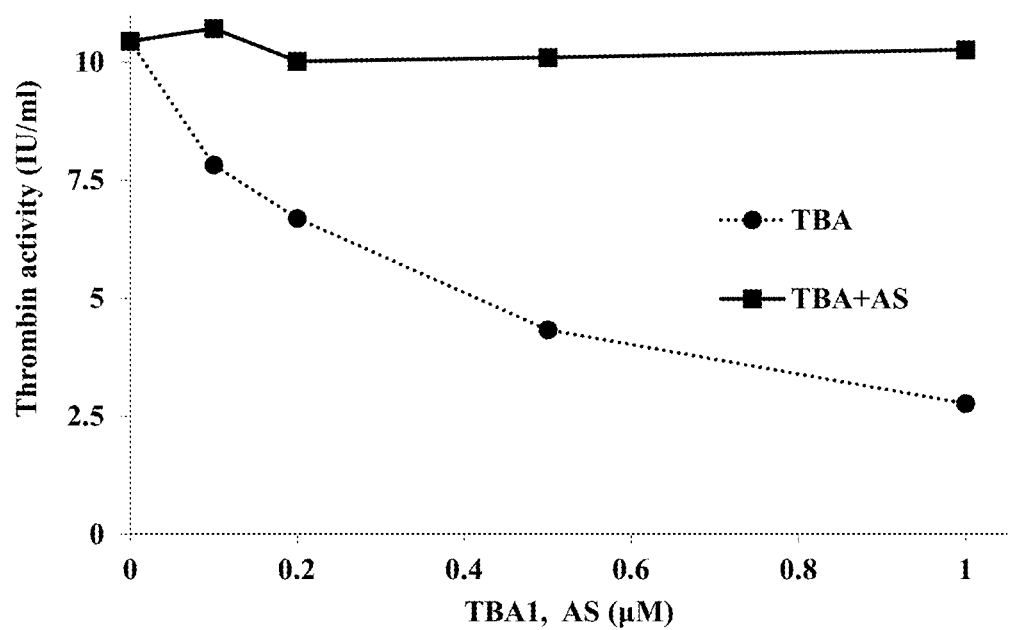

Specification includes a Sequence Listing.

(56) References Cited

OTHER PUBLICATIONS

Dougan, H. et al., 'Extending the Lifetime of Anticoagulant Oligodeoxynucleotide Aptamers in Blood' Nucl Med Biol. (2000) 27(3) pp. 289-297.

Fisher et al., 'Inhibition of MDR1 expression with altritol-modified siRNAs' 2007, NAR 35(4):1064-1074.

Griffin et al., 'In vivo anticoagulant properties of a novel nucleotide-based thrombin inhibitor and demonstration of regional anticoagulation in extracorporeal circuits' (1993) Blood 81 pp. 3271-3276.

Herdewijn, P. et al., 'Properties of Oligonucleotides with Six Membered Carbohydrate Mimics and a 1,4-Relationship Between the Base Moiety and the Hydroxymethyl Group' (1999) Nucleosides & Nucleotides 18 pp. 1371-1376.

Hermanson, G.T. et al *Immobilization Affinity Ligand Techniques* (1992) Academic Press, Inc. San Diego, USA pp. 1-45.

Krishnaswamy, S. "The transition of prothrombin to thrombin" J Thromb Haemost. Jun. 2013;11 Suppl 1 pp. 265-276.

Marino, F, "Engineering thrombin for selective specificity toward protein C and PAR1" J Biol Chem. 2010, 285(25):19145-52.

Pozzi, N., et al., 'Rigidification of the autolysis loop enhances Na(+) binding to thrombin' Biophys Chem. (2011) 159(1) pp. 6-13.

Rydel, T.J., et al., 'Crystallographic structure of human gamma-thrombin' J Biol Chem. (1994) 269(35) pp. 22000-22006.

Scaringe, S.A. et al. Chemical synthesis of biologically active oligoribonucleotides using β-cyanoethyl protected ribonucleoside phosphoradmidites Nucleic Acids Res. (1990) 18 pp. 5433-5441.

Song, H., et al 'Hemostatic Efficacy of Biological Self-Assembling Peptide Nanofibers in a Rat Kidney Model' Macromol Biosci. (2010)10 (1) pp. 33-39.

Tasset, D.M. et al 'Oligonucleotide Inhibitors of Human Thrombin that Bind Distinct Epitopes' (1997) J Mol Biol. 272(5) pp. 688-698.

Usman, N. et al., 'Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethionine tRNA' J. Am. Chem. Soc. (1987) 109 pp. 7845-7854.

Wincott, F. et al. 'Synthesis, deprotection, anaylysis and purification of RNA and ribozymes' Nucleic Acids Res. (1995) 23 pp. 2677-2684.

Wincott et al., 'A Practical Method for the Production of RNA and Ribozymes' (1997) Methods Mol. Bio., vol. 74 pp. 59-68.

Yang, L., et al 'Heparin-activated antithrombin interacts with the autolysis loop of target coagulation proteases' Blood (2004) 104(6) pp. 1753-1759.

Bompiani, et al., A High Affinity, Antidote-Controllable Prothrombin and Thrombin-Binding RNA Aptamer Inhibits Thrombin Generation and Thrombin Activity, J Thromb Haemost, 2012, pp. 870-880, vol. 10, No. 5.

Li, et al., Detection of protein Biomarkers using RNA Apatamer Microways and Enzymatically amplified surface plasmon resonance Imaging, Analytical Chemistry, Feb. 1, 2007, pp. 1082-1088, vol. 79 Issue 3.

Muller, et al., Anticoagulant Characteristics of HD1-22, a Bivalent Aptamer that Specifically Inhibits Thrombin and Prothrombinase, Journal of Thrombosis and Haemostasis, 2008, pp. 2105-2112, vol. 6.

Musumeci, et al., Polyvalent Nucleic Acid Aptamers and Modulation of their Activity: a focus on the thormbin binding aptamer, Pharmacology & Therapeutics, 2012, pp. 202-215, vol. 136.

\* cited by examiner

STABILIZED THROMBIN

CROSS-REFERENCE TO RELATED APPLICATION

This application is a divisional application of U.S. application Ser. No. 14/830,984 filed on Aug. 20, 2015, which claims priority to U.S. Provisional Application Ser. No. 62/039,989 filed Aug. 21, 2014 and claims benefit of Israel Patent Application Serial No. 234246 filed Aug. 21, 2014, the complete disclosure of which is hereby incorporated herein by reference for all purposes.

SEQUENCE LISTING

The instant application contains a Sequence Listing, which is submitted concomitantly with this application via EFS-Web in ASCII format and is hereby incorporated by reference in its entirety. Said ASCII copy, created on Aug. 11, 2014 is named "Sequence Listing" and is 3 kilobytes in size.

FIELD OF THE INVENTION

Provided herein are compounds, compositions comprising same and methods useful for reversibly stabilizing thrombin activity and extending thrombin's shelf-life. In particular, disclosed herein are reversible thrombin binding oligonucleotides capable of interacting with thrombin and inhibiting thrombin activity and an antisense oligonucleotide thereto, and compositions and methods of use therefore to stabilize thrombin activity in a liquid thrombin formulation.

BACKGROUND

Thrombin is a serine protease which serves as an active component in several hemostasis products. For example, fibrin sealants typically comprise a fibrinogen component and a thrombin component. When both components are mixed (e.g. when applied to a bleeding wound or surgical incision) thrombin cleaves fibrinogen and a fibrin polymer is formed. Concentrated purified thrombin in liquid form displays a reduction in activity during prolonged storage, primarily as a result of autolysis.

Hemostatic formulations containing liquid thrombin have special handling requirements in order to maintain thrombin's biologic activity and prevent autolytic degradation. For example, liquid thrombin requires freezing or the addition of protease inhibitors to maintain shelf-life stability. The shortcoming of the liquid thrombin solutions in use today are manifold: In the clinic and operating room, freezing is expensive and not always feasible, and promiscuous protease inhibitors may adversely affect activity of thrombin and other proteases in the hemostasis pathway once the fibrin sealant or the thrombin is applied.

Liquid thrombin preparations may be made into a lyophilized medical preparation, which is used after dissolving at the time of use. However, liquid preparations are advantageous compared with the lyophilized preparations in that they can be easily administered without the additional step of dissolving in a solvent prior to use. Also, the lyophilization step is costly and time consuming and may result in loss of yield.

Known compositions and methods for stabilizing thrombin are unsatisfactory and include the following: inclusion of various non-specific components (e.g. bulk carrier proteins such as albumins, different stabilizing sugars, general protease inhibitors etc.); formulation of the thrombin with inhibitors of thrombin activity, which although may be efficient, also inactivate or inhibit the thrombin, thereby reducing its effectiveness; and formulation of a low thrombin concentration solution, thereby necessitating administration of larger amounts of the formulation.

Several publications relate to stabilization of thrombin: for example International Patent Application Publication No. WO2008157304; U.S. Pat. Nos. 4,409,334; 7,351,561 and 8,394,372; U.S. Patent Application No. 20080311104; and European Patent Nos. EP0277096 B1 and EP 0478827 B1.

There remains a need for thrombin specific compounds useful to stabilize thrombin from autolytic degradation. Preferably, the compounds are reversible thrombin inhibitors which may be used with a concentrated liquid thrombin formulation.

SUMMARY OF THE INVENTION

Provided herein is a method for the use of thrombin binding oligonucleotides that have the exceptional ability to reversibly inhibit thrombin and stabilize its activity in an aqueous solution.

The thrombin binding oligonucleotides are such that they can bind to thrombin in a thrombin aqueous solution and inhibit, at least partially, the activity of thrombin. This inhibition of the thrombin activity by the thrombin binding oligonucleotide can be reversed by contacting the thrombin solution comprising the thrombin binding oligonucleotide with an antisense oligonucleotide. Thus, an aqueous thrombin solution can be stabilized by contacting it with the thrombin binding oligonucleotide in the absence of the antisense oligonucleotide. When the use of thrombin is desired, the activity of thrombin can be restored by contacting the stabilized thrombin solution with the antisense oligonucleotide. The reversibility of the binding of the thrombin binding oligonucleotide to thrombin by adding an antisense oligonucleotide provides an unequivocal advantage in the clinic and precludes the need to freeze and thaw a liquid thrombin solution or to reconstitute a lyophilized thrombin component prior to use.

The present inventors have shown for the first time that thrombin binding oligonucleotides are capable of reversibly inhibiting and stabilizing activity of liquid thrombin and that such molecules are useful in extending the shelf-life of thrombin.

Without wishing to be bound to theory, the thrombin binding molecules bind thrombin to inhibit, fully or partially, thrombin autolysis. Once the thrombin-binding oligonucleotide bound to thrombin comes in contact with an antisense oligonucleotide, the thrombin is released from inhibition and is capable of cleaving its heterologous substrates, including fibrinogen. The methods are further beneficial in that they are easily carried out in the clinic.

In one aspect, provided herein is a method for stabilizing thrombin activity in a solution (e.g. aqueous solution), the method includes inhibiting thrombin activity by contacting the thrombin with a thrombin binding oligonucleotide, wherein the thrombin binding oligonucleotide is capable of binding a second oligonucleotide; and wherein the inhibition of thrombin activity can be reversed by contacting the thrombin binding oligonucleotide with the second oligonucleotide. In some embodiments, the second oligonucleotide is an antisense oligonucleotide to the thrombin binding oligonucleotide.

In one aspect, provided herein is a method for stabilizing thrombin activity in a solution, the method includes inhibiting thrombin activity by contacting the thrombin with a thrombin binding oligonucleotide, wherein the thrombin binding oligonucleotide is capable of binding an antisense oligonucleotide; and wherein the inhibition of thrombin activity can be reversed by contacting the thrombin binding oligonucleotide bound to thrombin with the antisense oligonucleotide.

In some embodiments of the method, the solution comprises a thrombin concentration equal to or higher than 4 IU/ml and up to 15,000 IU/ml thrombin. In some embodiments, the thrombin concentration in solution is 10 IU/ml-1,000 IU/ml; 20 IU/ml-15,000 IU/ml; 100 IU/ml-5,000 IU/ml; 200 IU/ml-1000 IU/ml or 300 IU/ml-1000 IU/ml.

The thrombin binding oligonucleotide is selected to bind to any region of the thrombin to which binding would inhibit thrombin activity in a reversible manner; for example to inhibit thrombin activity from autolysis. In some embodiments, the thrombin binding oligonucleotide binds to exosite I or exosite II of thrombin or to both. In specific embodiments of the method, the thrombin binding oligonucleotide binds to exosite I. In some embodiments, the thrombin binding oligonucleotide is an aptamer comprising a DNA and/or RNA nucleotide sequence of about 10 to about 60 nucleotides in length, or about 12 to about 40 nucleotides in length, about 14 to about 35 nucleotides in length, or about 14 to about 25 nucleotides in length. The aptamer may bind to a consecutive linear sequence of amino acids in thrombin or may bind to a three dimensional region of thrombin. In some embodiments, the thrombin binding aptamer is a DNA oligonucleotide comprising a nucleotide sequence set forth in SEQ ID NO:1 5' GGTTGGTGTGGTTGG 3', a variant of SEQ ID NO:1 comprising a nucleotide sequence set forth in SEQ ID NO:2 5' GGGTTGGGTGTGGGTTGGG 3' or a DNA oligonucleotide comprising a nucleotide sequence set forth in SEQ ID NO:3 5' AGTCCGTGGTAGGGCAGGTTGGGGTGACT 3'. In specific embodiments, the nucleotide sequence of the thrombin binding aptamer is set forth in SEQ ID NO:1. In some embodiments, the nucleotide sequence of the thrombin binding aptamer is set forth in SEQ ID NO:2. In some embodiments, the nucleotide sequence of the thrombin binding aptamer is set forth in SEQ ID NO:3.

In some embodiments, the thrombin binding aptamer is an RNA oligonucleotide comprising a nucleotide sequence set forth in SEQ ID NO:4 5' GGUUGGUGUGGUUGG 3', a variant of SEQ ID NO: 4 comprising a nucleotide sequence set forth in SEQ ID NO:5 5'GGGUUGGGUGUGG-GUUGGG 3' or an RNA oligonucleotide comprising a nucleotide sequence set forth in SEQ ID NO:6 5' AGU-CCGUGGUAGGGCAGGUUGGGGUGACU 3'.

The antisense oligonucleotide is selected to bind to the thrombin binding oligonucleotide. The antisense oligonucleotide includes a nucleotide sequence that binds to the thrombin binding oligonucleotide and may bind to a consecutive linear sequence or to a three dimensional structure of the thrombin binding oligonucleotide. In some embodiments of the method, the antisense oligonucleotide comprises a DNA and/or RNA nucleotide sequence of about 8 to about 60 nucleotides in length, or about 10 to about 40 nucleotides in length, about 12 to about 35 nucleotides in length, or about 12 to about 25 nucleotides in length. The antisense oligonucleotide may bind part of or the entire thrombin binding oligonucleotide. In some embodiments, the antisense oligonucleotide is a DNA oligonucleotide having a nucleotide sequence set forth in SEQ ID NO:7 5' CCAACCACACCAACC 3', SEQ ID NO:8 5' CCCAACC-CACACCCAACCC, or SEQ ID NO:9 5' AGTCACCC-CAACCTGCCCTACCACGGACT 3'. In some embodiments, the antisense oligonucleotide is an RNA oligonucleotide having a nucleotide sequence set forth in SEQ ID NO:10 5' CCAACCACACCAACC 3', SEQ ID NO:11 5' CCCAACCCACACCCAACCC 3' or SEQ ID NO:12 5' AGUCACCCCAACCUGCCCUACCACGGACU 3'.

An antisense oligonucleotide can further be covalently or non-covalently attached to or associated with a molecule which may include one or more of a nucleotide or non-nucleotide moiety, e.g. a nucleotide, a nucleotide analog, an amino acid, a peptide, a polypeptide, a lipid moiety, a carbohydrate moiety, a marker, a matrix, beads or a tag, directly or using a linker In some embodiments of the method, the solution comprises a molar ratio of less than about 10:1 to about 1:1 thrombin binding oligonucleotide:thrombin. In some embodiments, the ratio of the thrombin binding oligonucleotide:thrombin in the solution is about 9:1, or about 8:1, or about 7:1, or about 6:1, or about 5:1, or about 4:1, or about 3.5:1, or about 3:1, or about 2.5:1; or about 2:1 or about 1:1.

In some embodiments of the method, dissociation constant (Kd) between the thrombin binding oligonucleotide and the antisense oligonucleotide in solution is equal to or less than 0.2 µM (microM).

In another aspect, provided herein is a thrombin formulation for use in applications requiring conversion of fibrinogen to fibrin, the formulation comprising: thrombin and a thrombin binding oligonucleotide, wherein the thrombin binding oligonucleotide inhibits thrombin activity and is capable of binding an antisense oligonucleotide and wherein the inhibition of thrombin activity can be reversed by contacting the formulation with the antisense oligonucleotide.

In some embodiments of the formulation, thrombin is present in the formulation at a concentration equal to or higher than 4 IU/ml and up to 15,000 IU/ml thrombin. In some embodiments, the thrombin concentration in solution is 10 IU/ml-1,000 IU/ml; 20 IU/ml-15,000 IU/ml; 100 IU/ml-5,000 IU/ml; 200 IU/ml-1000 IU/ml or 300 IU/ml-1000 IU/ml.

The thrombin binding oligonucleotide is selected to bind to any region of the thrombin to which binding would reversibly inhibit and stabilize thrombin activity; for example fully or partially inhibit thrombin activity from autolysis. In some embodiments of the formulation, the thrombin binding oligonucleotide binds to exosite I or exosite II of thrombin. In specific embodiments, the thrombin binding oligonucleotide binds to exosite I. In some embodiments, the thrombin binding oligonucleotide is an aptamer comprising a nucleic acid sequence set forth in any of SEQ ID NOS:1-6. In one embodiment the thrombin binding oligonucleotide is an aptamer comprising a nucleic acid sequence set forth in SEQ ID NO:1.

In some embodiments of the formulation, the thrombin binding oligonucleotide and thrombin are present at a molar ratio of less than about 10:1 to about 1:1 thrombin binding oligonucleotide:thrombin. In some embodiments, the ratio of the thrombin binding oligonucleotide:thrombin in the formulation is about 9:1, or about 8:1, or about 7:1, or about 6:1, or about 5:1, or about 4:1, or about 3.5:1, or about 3:1, or about 2.5:1; or about 2:1 or about 1:1.

In some embodiments of the formulation, the dissociation constant (Kd) between the thrombin binding oligonucleotide and the antisense oligonucleotide in solution is equal to or less than 0.2 μM (microM).

In yet another aspect, provided herein is a kit comprising a container comprising thrombin and a thrombin binding oligonucleotide; a container comprising an antisense oligonucleotide to the thrombin binding oligonucleotide; and optionally instructions for use.

The containers can be a monolithic piece including at least two chambers separated by a septum.

In one embodiment, the chambers are divided by a septum, which is at least partially breakable, braking the septum allows mixing the oligonucleotide inhibited thrombin and the antisense oligonucleotide.

In some embodiments, the container and/or chambers are flexible and breaking the septum can be achieved by applying pressure (e.g. manual pressure) onto the container and/or chambers.

The size of each chamber and fill volumes are dependent e.g. on the intended use, suitable concentration ratios between the antisense oligonucleotides, and the thrombin binding oligonucleotide, and/or desired volume.

The container and/or chamber can comprise an opening e.g. including Male or Female Luer Lock. The opening can be resealable.

The antisense oligonucleotide can be in powder or liquid form. The kit can contain a liquid for reconstitution.

The kit can comprise a multi—e.g. dual chamber prefilled syringe, one chamber containing thrombin and a thrombin binding oligonucleotide and the other chamber containing an antisense oligonucleotide e.g. a dual chamber as described in PCT Patent Publication No. WO 97/46202A1.

In some embodiments of the kit, the thrombin binding oligonucleotide is capable of binding the antisense oligonucleotide and the binding of the thrombin binding oligonucleotide and the thrombin is reversed by contacting the thrombin binding oligonucleotide with the antisense oligonucleotide. In some embodiments, the antisense oligonucleotide is in solution. In alternative embodiments, the antisense oligonucleotide is solid phase or is linked to a solid phase. The kit may further comprise a container comprising fibrinogen. In various embodiments of the kit, the antisense oligonucleotide is excluded from the fibrinogen component.

In some embodiments of the kit, the thrombin binding oligonucleotide and thrombin are present at a molar ratio of less than about 10:1 to about 1:1 thrombin binding oligonucleotide:thrombin. In some embodiments, the ratio of the thrombin binding oligonucleotide:thrombin in the formulation is about 9:1, or about 8:1, or about 7:1, or about 6:1, or about 5:1, or about 4:1, or about 3.5:1, or about 3:1, or about 2.5:1; or about 2:1 or about 1:1.

Within one embodiment, the containers are sealed containers having a label affixed to an exterior surface thereof. In some embodiments, the formulation is prepared for use as a fibrin sealant component. The kit may further comprise one or more devices for the delivery of the thrombin-thrombin binding oligonucleotide; antisense oligonucleotide and/or the fibrinogen components.

In another aspect, provided is a method for converting fibrinogen to fibrin comprising:

mixing a formulation comprising: thrombin and a thrombin binding oligonucleotide, wherein the thrombin binding oligonucleotide is capable of inhibiting thrombin activity and of binding an antisense oligonucleotide, and wherein the inhibition of thrombin activity is reversed by the addition of the antisense oligonucleotide; the antisense oligonucleotide and fibrinogen.

In some embodiments of the method, the ratio between the antisense oligonucleotide and the thrombin binding oligonucleotide is in the range of about 1:1 to 2:1.

In some embodiments of the method, the thrombin binding oligonucleotide and thrombin are present at a molar ratio of less than about 10:1 to about 1:1 thrombin binding oligonucleotide:thrombin. In some embodiments, the ratio of the thrombin binding oligonucleotide:thrombin in the formulation is about 9:1, or about 8:1, or about 7:1, or about 6:1, or about 5:1, or about 4:1, or about 3.5:1, or about 3:1, or about 2.5:1; or about 2:1 or about 1:1. Fibrinogen component can be prepared as described in the art, for example, in PCT Patent Publication No. WO 93/05822 or as in the fibrin kit described in the European pharmacopeia. In some embodiments, the fibrinogen component is free of or is depleted of plasmin(ogen) as disclosed in U.S. Pat. No. 7,641,918 or in PCT Patent Publication No. WO 02/095019.

In some embodiments of the method, the nucleic acid sequence of the thrombin binding oligonucleotide is set forth in any of SEQ ID NOS:1-6, preferably SEQ ID NO:1.

In yet another aspect, provided herein is an antisense oligonucleotide of a thrombin binding oligonucleotide for use in reversing a binding between the thrombin binding oligonucleotide and thrombin in applications requiring converting fibrinogen to fibrin.

In some embodiments, the antisense oligonucleotide comprises any of SEQ ID NOS:7-12. Further provided is a composition comprising the antisense oligonucleotide disclosed herein; and a pharmaceutically acceptable carrier.

In another aspect, provided herein is a method of screening for oligonucleotides capable of reversibly binding and stabilizing thrombin activity and of binding an antisense oligonucleotide. Accordingly, provided is a method for screening for an oligonucleotide capable of reversibly binding and stabilizing the activity of thrombin in an aqueous liquid thrombin formulation, comprising a. contacting thrombin or a fragment thereof, each exhibiting an initial activity of 4 to 15,000 IU/ml, with a set of test thrombin binding oligonucleotides; and identifying one or more thrombin binding oligonucleotides which inhibit, at least partially, the initial activity; and b. contacting the thrombin bound oligonucleotide of step a) with a set of test antisense oligonucleotides;

whereby restoration of at least 4 IU/ml thrombin activity following step (b) indicates 1) a potential thrombin binding oligonucleotide for thrombin stabilization and 2) a potential antisense oligonucleotide to reverse the inhibitory effect of the thrombin binding oligonucleotide.

In some embodiments of the screening method, the thrombin has an initial activity of 4 to 15,000 IU/ml, about 20 IU/ml to 15,000 IU/ml, or 100 IU/ml to 5,000 IU/ml, 200 IU/ml to about 1000 IU/ml or about 300 IU/ml to about 1000 IU/ml.

In some embodiments the method provides an antisense oligonucleotide that restores thrombin activity to at least 4 IU/ml, at least about 20 IU/ml, at least about 100 IU/ml or at least about 300 IU/ml, at least about 1000 IU/ml and up to 1500 IU/ml of the initial activity of thrombin.

Figure 4A:
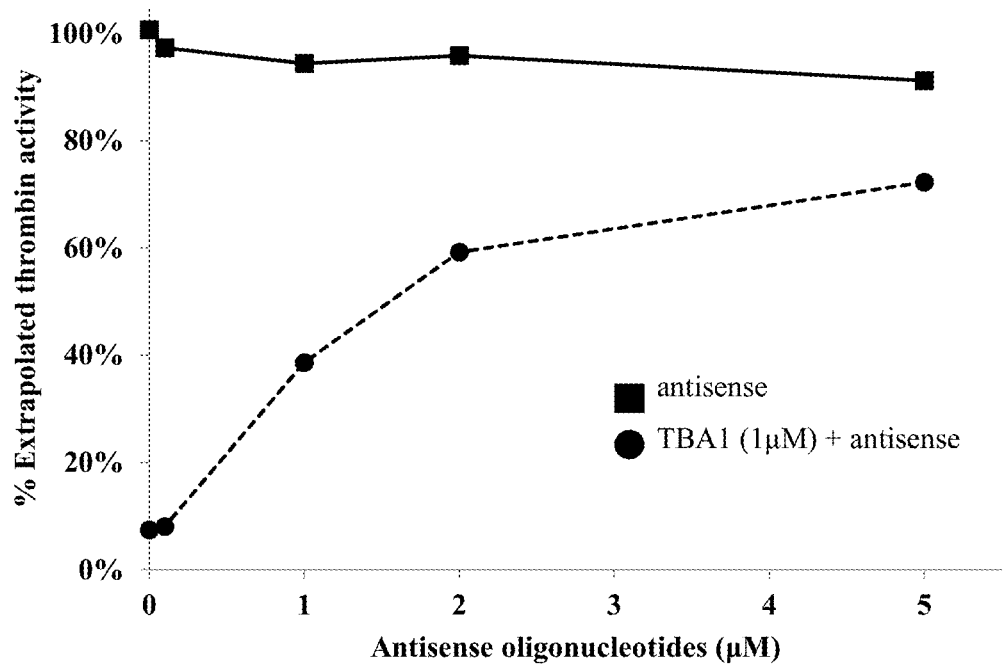
Figure 4B:
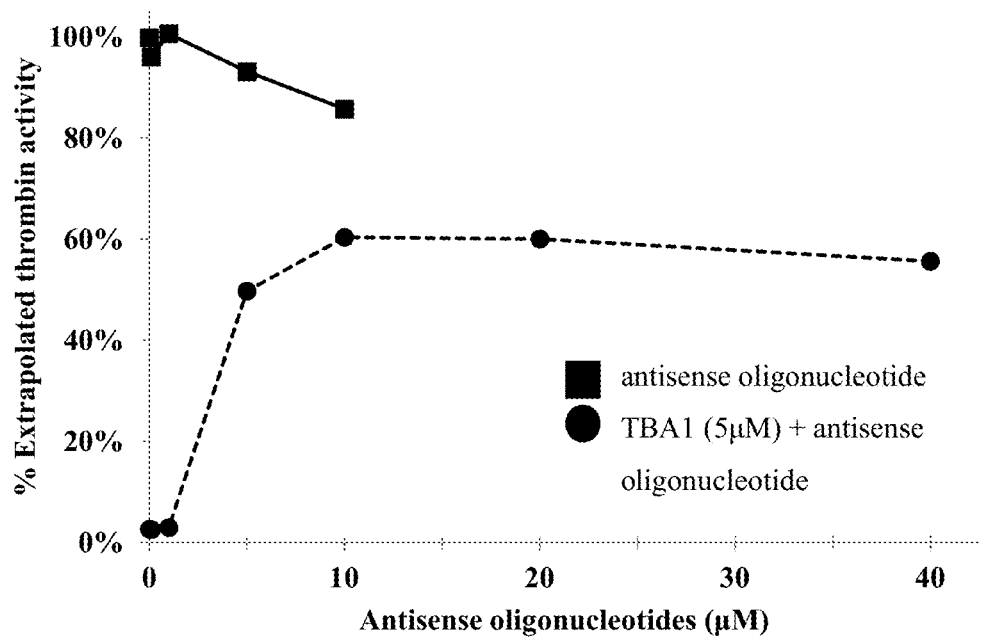

In an alternative, provided is a method for screening for an oligonucleotide capable of reversibly binding and stabilizing the activity of thrombin in an aqueous liquid thrombin formulation, comprising a. contacting thrombin or a fragment thereof, each exhibiting an initial activity, with a set of test thrombin binding oligonucleotides; and identifying one or more thrombin binding oligonucleotides which inhibit, at least 60% of the initial activity; and b. contacting a thrombin bound oligonucleotide of step a) with a set of test antisense oligonucleotides;

whereby restoration of more than 40% of the initial activity following step (b) indicates 1) a potential thrombin binding oligonucleotide for thrombin stabilization and 2) a potential antisense oligonucleotide to reverse the inhibitory effect of the thrombin binding oligonucleotide.

In some embodiments, the method provides stabilizing thrombin activity and restoring at least, 40%, 50% and up to 100% of the initial activity of thrombin.

In another aspect, provided herein is an antisense oligonucleotide of a thrombin binding oligonucleotide for use in reversing thrombin inhibition by thrombin binding oligonucleotide in applications requiring converting fibrinogen to fibrin.

In some embodiments, the antisense oligonucleotide is bound to a solid phase.

In another aspect, provided herein is a method for reversing an oligonucleotide inhibited thrombin, the method comprising the steps of contacting the oligonucleotide inhibited thrombin with an antisense to the oligonucleotide. In one embodiment, the antisense to the oligonucleotide is immobilized on a solid phase.

In some embodiments, the antisense is bound to the solid phase directly or indirectly.

In some embodiments, the solid phase is selected from the group consisting of chromatographic media beads and filters.

In all aspects herein, the thrombin binding oligonucleotides are not used as anticoagulants.

In another aspect, the invention relates to a delivery applicator comprising:

a barrel holding an oligonucleotide inhibited thrombin; and a vessel having a delivery opening and holding an antisense oligonucleotide linked to a solid phase;

wherein the barrel and the vessel are capable of being in fluid communication, so that after fluid communication and contact of the inhibited thrombin with the solid phase, thrombin activity is increased before delivering thrombin through the delivery opening.

In some embodiments, the fluid communication is via a re-sealable opening positioned between the barrel and the vessel.

In some embodiments, the delivery applicator further comprises a barrel having a delivery opening and holding fibrinogen.

In another aspect, the invention relates to a delivery applicator comprising:

a barrel holding an oligonucleotide inhibited thrombin; and a vessel having a delivery opening and holding an antisense oligonucleotide;

wherein the barrel and the vessel are capable of being in fluid communication, so that after fluid communication and contact of the inhibited thrombin with the antisense, thrombin activity is increased before delivering thrombin through the delivery opening.

In another aspect, the invention relates to a delivery applicator comprising:

a barrel holding an oligonucleotide inhibited thrombin; and an antisense oligonucleotide, wherein the oligonucleotide inhibited thrombin and the antisense oligonucleotide are held in separate chambers that are capable of being in fluid communication, so that allowing fluid communication between the chambers and contact between the inhibited thrombin and the antisense results in increased thrombin activity before delivery, and wherein the barrel has an opening for delivery therethrough of the thrombin.

In another aspect, the invention relates to a delivery applicator comprising:

a container holding an oligonucleotide inhibited thrombin; and an antisense oligonucleotide linked to a solid phase, wherein the oligonucleotide inhibited thrombin and the antisense oligonucleotide are held in separate chambers that are capable of being in fluid communication, so that fluid communication between the chambers and contact between the inhibited thrombin and the solid phase results in increased thrombin activity before delivery, and wherein the container has a re-sealable opening for delivery therethrough of the thrombin.

Re-sealable opening is an opening sealed by e.g. a membrane, cap, needle, rubber cap, stent, delivery tube and/or tip.

In one embodiment, a re-sealable opening prevents or minimizes leakage of liquid.

In some embodiments, the delivery applicator further comprises a container having a delivery opening and holding fibrinogen.

In some embodiments, the inhibited thrombin, fibrinogen and/or the formulations can be in solid, dry, aqueous, and/or frozen form. The solid phase can be dry or suspended in liquid, e.g. buffers.

In some embodiments the kits, device, containers, chambers, vessel, delivery application, barrel and/or syringe etc. may comprise an aqueous liquid for reconstitution.

An oligonucleotide inhibited thrombin is a thrombin combined with an oligonucleotide, said oligonucleotide can bind to thrombin in a thrombin aqueous solution, and thrombin activity is inhibited by the oligonucleotide, at least partially.

These and other aspects and embodiments of the invention will become evident upon reference to the following detailed description of the invention and the figures.

BRIEF DESCRIPTION OF THE FIGURES

FIG. 1 is a graph showing that the antisense oligonucleotide (AS) effectively counteracts TBA1 (Thrombin Binding Aptamer 1) inhibition of thrombin. Specifically, TBA1 inhibits 10 IU/ml (~0.1 μM) thrombin in a dose dependent manner. Equimolar antisense treatment completely restores activity (as measured by a clotting assay).

FIG. 2A-2D are graphs representing thrombin stabilization by TBA1, over time and at different temperatures. TBA1 was added to thrombin (~1000 IU/ml) at the indicated concentrations and incubated at RT for up to 90 days (2A) at 37° C. for up to 14 days (2B) or at 2-8° C. for up to 180 days (2C). The binding of TBA1 was reversed with an equimolar concentration of antisense oligonucleotide, and diluted 100-fold for testing the activity of the remaining thrombin tested using the clotting assay. (2D): Remaining thrombin activities after incubation at 37° C. for 7 days in the presence of different TBA1 concentrations as in FIG. 2B are plotted against TBA1 concentrations (μM).

FIG. 3 is a bar graph showing similar elasticity of a control clot, and a clot formed at the presence of 25 μM TBA1+25 μM antisense oligonucleotide.

FIGS. 4A and 4B are graphs showing that TBA1 cannot be fully reversed with antisense within the time frame required for thrombin to clot a fibrinogen solution. FIG. 4A:

TBA1 is neutralized with increasing amounts of antisense oligonucleotides and thrombin activity tested in a thrombin activity assay. Increasing the antisense:TBA1 ratio above 1:1 results in increasing recovery of thrombin activity, but 100% recovery cannot be reached. FIG. 4B: TBA1 is neutralized with up to 40 μM antisense (antisense:TBA1 ratios=1-4) in the same setting peaks at 60% recovery of thrombin activity, as measured by the thrombin activity assay. In both experiments, thrombin activity was tested immediately after addition of antisense oligonucleotide and mixing.

Figure 5:
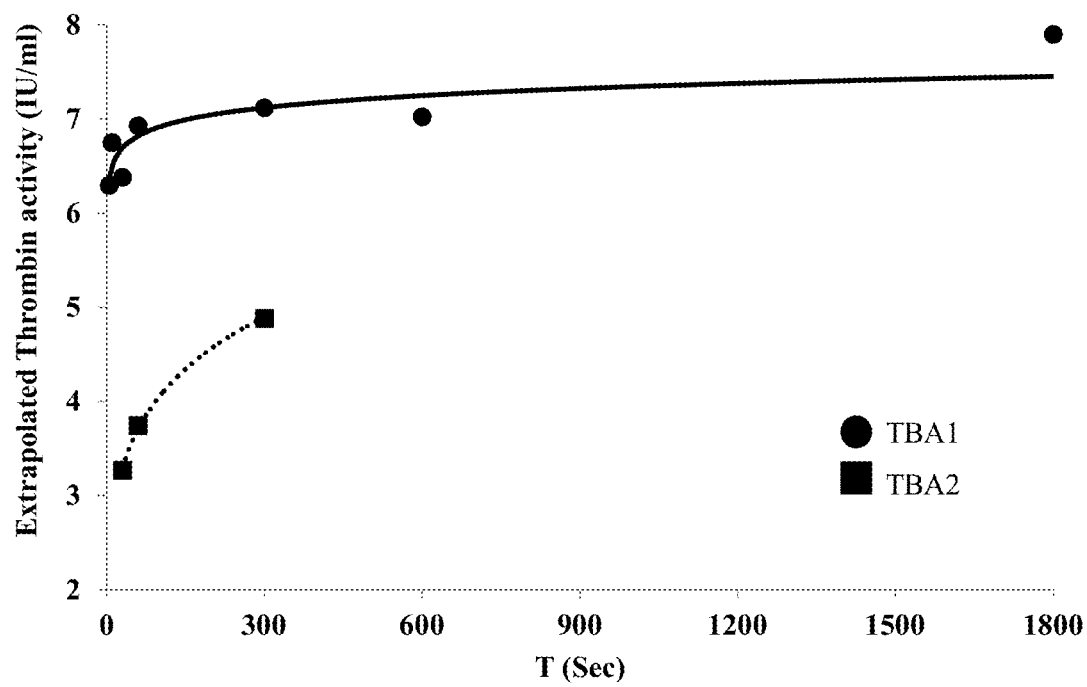

FIG. 5 is a graph showing time-dependent reversal of 2504 TBA-mediated inhibition with antisense oligonucleotides, with a low thrombin concentration (~0.1 μM). TBA inhibition at a large molar excess over thrombin (250:1) is not effectively neutralized with the antisense oligonucleotide even after 30 minutes.

Figure 6:
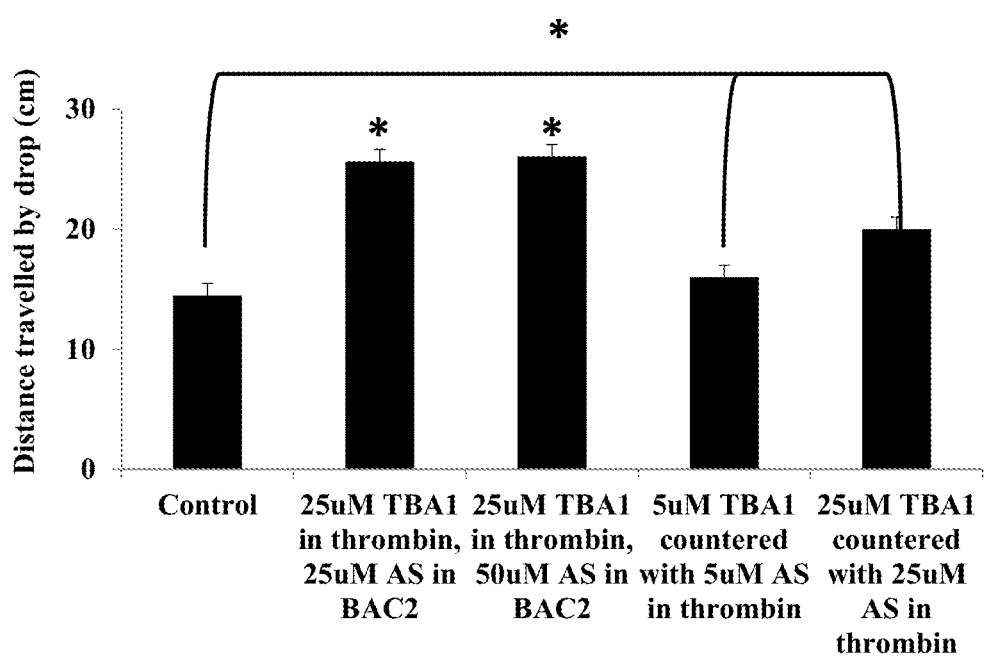

FIG. 6 is a bar graph showing validity of rapid neutralization of TBA1 with antisense oligonucleotides at optimized molar ratios in a drop test. Control was performed without TBA1 or antisense oligonucleotides. Experiments were conducted using different ratios of TBA1:antisense, when the antisense was added in a separate compartments or antisense was added directly to the thrombin component containing TBA at two concentrations.

Figure 7:
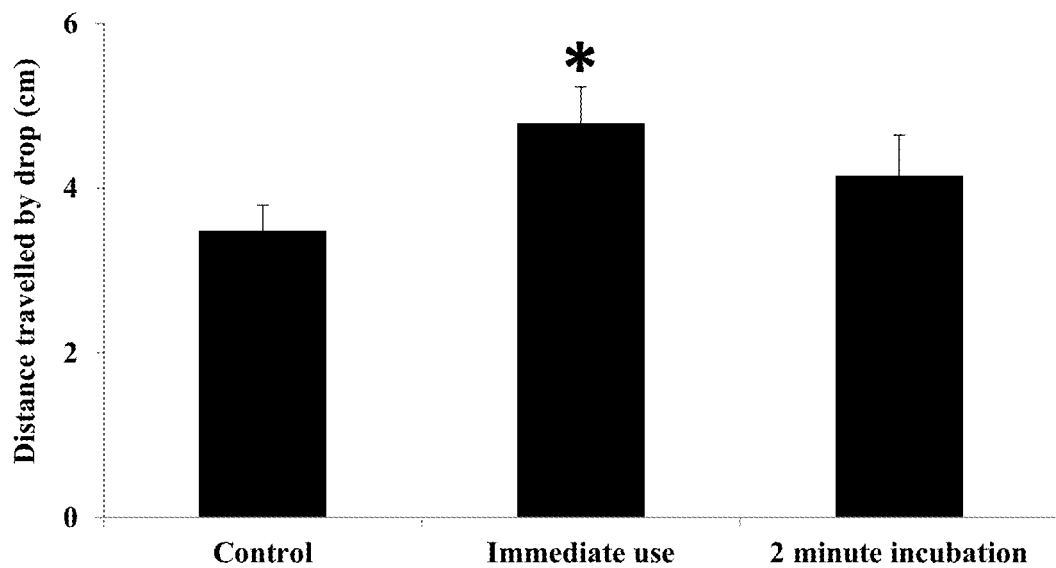

FIG. 7 is a bar graph showing that the kinetics of neutralization of 25 μM aptamer by antisense oligonucleotides is effective for use in a classical fibrin sealant setting (1000 IU/ml thrombin solution). A modified drop test shows that a two minutes pre-incubation of thrombin/TBA1 (25 μM) with equimolar antisense oligonucleotides is sufficient to reduce inhibition to non-significant levels of thrombin (1000 IU/ml).

Figure 8:
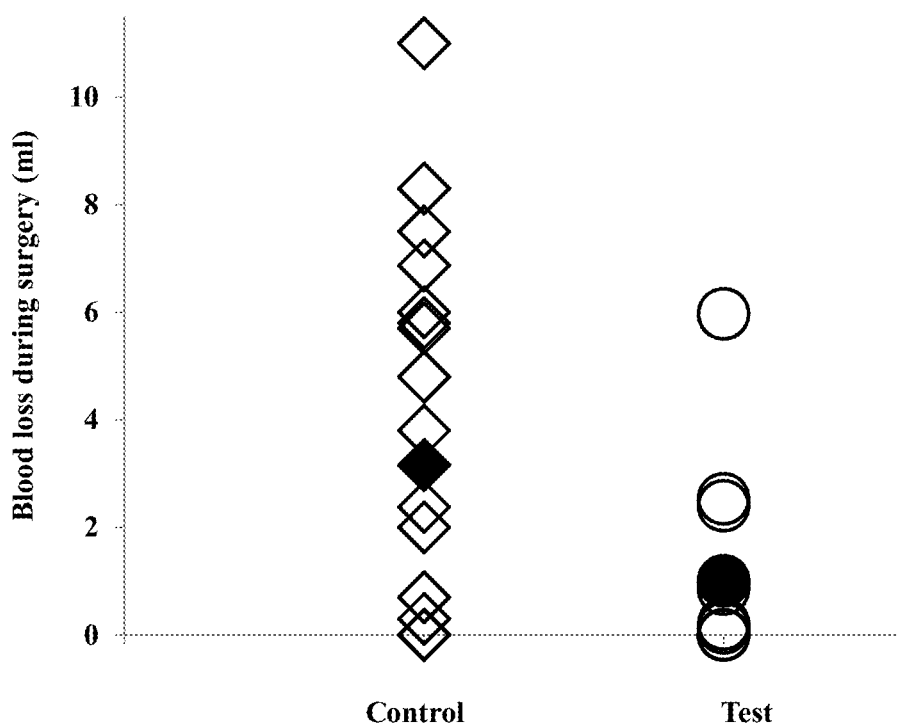

FIG. 8 shows that TBA1 added to the thrombin component in a two-component fibrin sealant can be efficiently reversed with antisense oligonucleotides added to the thrombin/TBA component in an in vivo setting. Results from the rat kidney hemostasis model show comparable hemostatic activity for thrombin (control) and TBA1-inhibited, antisense-neutralized thrombin (test). 25 μM TBA1 and antisense were used. An equimolar amount of antisense oligonucleotide was added to the thrombin just prior to the assembly of the EVICEL® device (fitted with a spray tip extension for application). The thrombin concentration is 1000 IU/ml. Full symbols: average value, open symbols: results for individual rats.

Figure 9A:
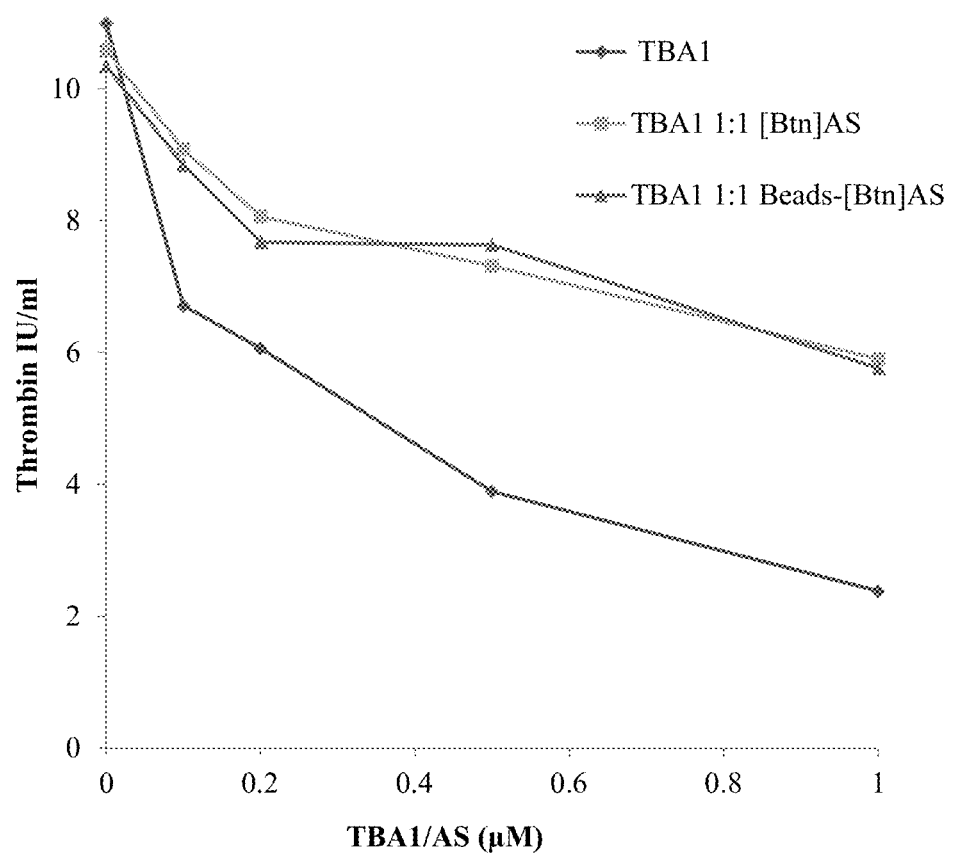

FIG. 9A shows the inhibition of thrombin mediated by TBA1 and the reversal inhibition mediated by antisense (AS) oligonucleotide bound to biotin or to biotin-streptavidin beads. Increasing amounts of TBA1 were added to ~0.1 μM (10 IU/ml) thrombin and thrombin activity was inhibited in a dose-dependent manner (diamonds). Addition of biotinylated antisense oligonucleotide at equimolar amounts/equal concentration to TBA1 restored thrombin activity up to ~40% of initial activity (squares). Addition of pre-incubated biotinylated antisense oligonucleotide with Sepharose-Streptavidin at the same concentrations resulted in similar thrombin activity restoration like with biotinylated TBA1 alone. Furthermore, addition of biotinylated beads alone at the highest concentration did not inhibit thrombin activity at all (not shown).

Figure 9B:
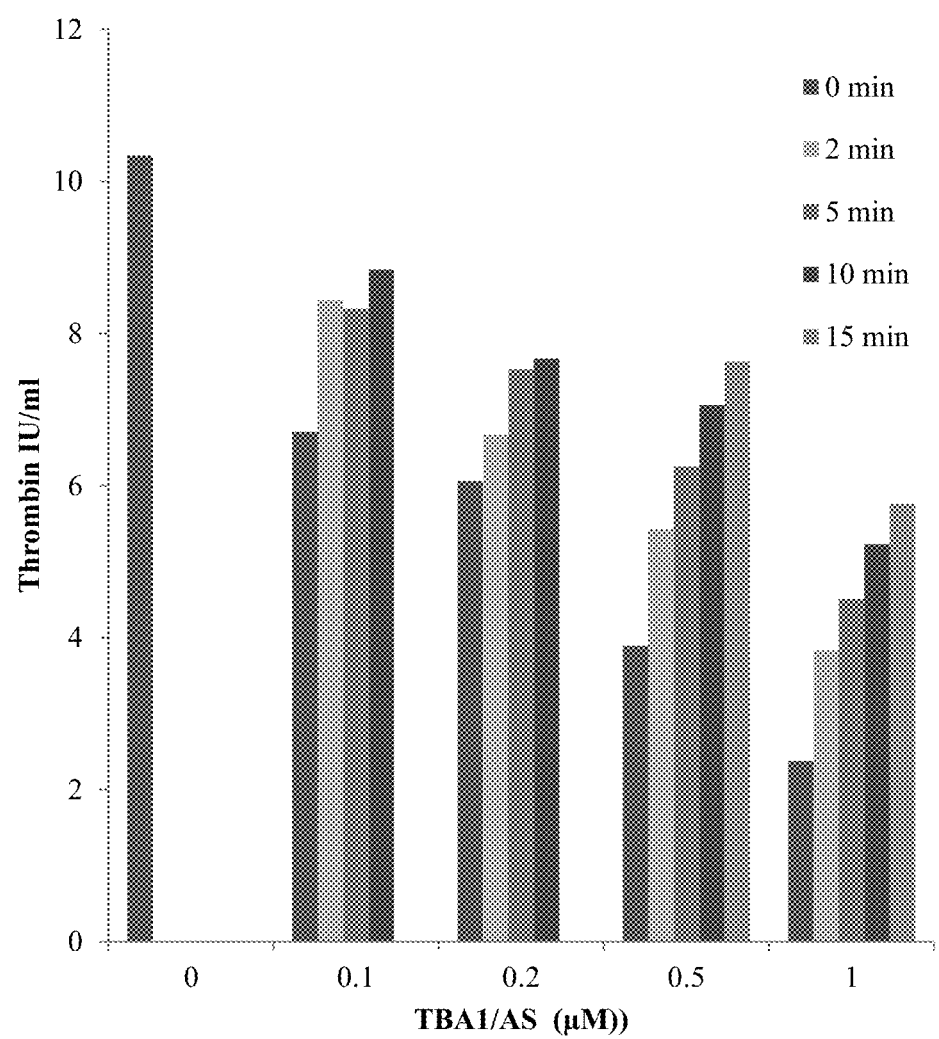

In FIG. 9B the biotinylated antisense oligonucleotide or the biotinylated antisense oligonucleotide pre-incubated with the Sepharose-Streptavidin was added to the reaction at least 15 minutes prior to the thrombin activity testing, thereby giving enough time for TBA1/biotinylated antisense oligonucleotide interaction, in FIG. 9B the time needed for maximal restoration of thrombin activity was assayed: biotinylated antisense oligonucleotide pre-incubated with the Sepharose-Streptavidin was added at the indicated time points prior to thrombin activity testing. The results show that higher TBA1 concentrations need longer time for reversing thrombin inhibition by biotinylated-AS than lower concentrations of TBA1 with corresponding concentration of biotinylated-AS.

DETAILED DESCRIPTION OF THE INVENTION

The present disclosure is based in part upon the finding that thrombin binding oligonucleotides developed for treating coagulation disorders are capable of reversibly inhibiting and stabilizing thrombin activity in a liquid thrombin formulation.

The terms "reversibly stabilizing thrombin activity" and "reversibly stabilizing thrombin" refer to reducing or preventing, in part or in full, thrombin autolytic activity in a manner that can be counteracted so as to permit thrombin to carry out its biological activity on heterologous substrates, including the conversion of fibrinogen to fibrin.

The term "thrombin fragment" includes an amino acid sequence of thrombin, linear or non-linear, that maintains thrombin activity, for example, thrombin autolytic activity and/or thrombin mediated fibrinogen cleavage.

Provided herein are methods of using isolated oligonucleotides that bind to thrombin for the inhibition and stabilization of thrombin activity. Further provided herein are thrombin formulations comprising thrombin and thrombin binding oligonucleotides and methods of reversing the inhibition of thrombin and uses thereof for converting fibrinogen to fibrin.

"Nucleotide" is meant to encompass a monomer of a nucleic acid, including but not limited to deoxyribonucleotides and/or ribonucleotides, which may be natural or synthetic, and or modified or unmodified. Modifications include changes to the sugar moiety, the base moiety and or the linkages between ribonucleotides in the oligoribonucleotide. Accordingly, as used herein, the term "deoxyribonucleotide" encompasses natural and synthetic, unmodified and modified deoxyribonucleotides and the term "ribonucleotide" encompasses natural and synthetic, unmodified and modified ribonucleotides.

The term "modified nucleotide" refers to nucleotides that have one or more non-naturally occurring substituents which function in a similar manner to natural nucleotides. Such modified nucleotides may be preferred over the naturally occurring forms because of desirable properties such as, for example, enhanced affinity for a target (e.g. protein target or antisense oligonucleotide) and enhanced nuclease stability. Non-limiting examples include 2' sugar modifications such as 2'O-methyl, 2'O-ethyl, 2'fluoro and the like; modified sugar moieties including bridged nucleic acids (for example, LNA and ENA disclosed in PCT Patent Publication No. WO 98/39352, WO 00/47599 and WO 99/14226) and altritol (for example, Allart, et al., 1998. Nucleosides & Nucleotides 17:1523-1526; Herdewijn et al., 1999. Nucleosides & Nucleotides 18:1371-1376; Fisher et al., 2007, NAR 35(4): 1064-1074); modified internucleotide linkages including phosphorothioate, phosphonocarboxylate and/or phosphinocarboxylate linkages (for example, U.S. Pat. Nos. 6,693,187 and 7,067,641).

"Oligonucleotide" refers to a deoxyribonucleotide sequence, a ribonucleotide sequence or a chimera of DNA and RNA from about 8 to about 60 nucleotides. Each DNA or RNA nucleotide forming the oligonucleotide may be independently natural or synthetic, and may be unmodified or modified (for example as described hereinabove). The nucleotide sequence of an oligonucleotide is written according to the conventional notation, with 5' terminus appearing on the left hand of the sequence and the 3' terminus appearing on the right hand thereof. Oligonucleotides may be provided as salts, for example a sodium salt.

By "complementarity" is meant that a nucleic acid can form hydrogen bond(s) with another nucleic acid sequence by the classic Watson-Crick bonding or other non-traditional bonding. Complementarity can be full or partial. As used herein, the thrombin binding oligonucleotide has complementarity to the antisense oligonucleotide.

As used herein, the term "aptamer" is a nucleic acid sequence that binds to a molecular target such as a small molecule, a peptide, a protein, and even a microorganism such as a virus or a bacteria. Aptamers are selected by incubating the target molecule with a large pool of binders such as oligonucleotides (usually about 10 to 60 mers). One of the methods for selection of oligonucleotide aptamers is called "systematic evolution of ligands by exponential enrichment" (SELEX) is generally used with modification and variations for the selection of specific aptamers.

In preferred embodiments disclosed herein, the aptamer is a DNA and/or RNA (DNA, RNA or chimera DNA/RNA) and includes unmodified and or modified nucleotides.

In some embodiments, the aptamer or a salt of such aptamer is an RNA or DNA single-strand oligonucleotides which bind to a target protein and do not generally exhibit non-specific effects. Aptamers can be modified for stability or other desired qualities in accordance with any nucleic acid modifications known to one of skill in the art.

Thioaptamers are aptamers which contain sulfur modifications at specific internucleoside phosphoryl sites, and may possess enhanced stability, nuclease resistance, target affinity and/or selectivity. Examples of thioaptamers include phosphoromonothioate (S-ODN) and phosphorodithioate (S2-ODN) oligodeoxy thioaptamers. Further information on aptamers and thioaptamers can be found in U.S. Pat. Nos. 5,218,088 and 6,423,493.

Thrombin Binding Aptamers (TBAs) are known for their potential use as anticoagulants. However, due to their short half-life in blood, their use has been shown not to be efficient (See Bock, et al., 1992. Nature. 1992 355(6360):564-6; Tasset and Kubik, 1997, J Mol Biol. 272(5):688-98; Dougan et al., 2000 27(3):289-97; DeAnda, et al., 1994 58(2):344-50; Griffen et al., 1993. Blood 81:3271-76; PCT Patent Publication Nos. WO2007/025049 and WO2010/033167).

Antisense oligonucleotides are single stranded DNA or RNA molecules or chimeras of DNA and RNA or DNA or RNA analogs of about 8 to about 60 nucleotides in length. As used herein, an antisense oligonucleotide comprises a sequence that is complementary to the thrombin binding oligonucleotide. The antisense oligonucleotide can be of the same length as the thrombin binding oligonucleotide. In some embodiments, the antisense oligonucleotides comprise additional residues, or may be a fragment thereof as long as they retain the binding affinity to the thrombin binding oligonucleotide to reverse the binding of the thrombin binding oligonucleotide to thrombin. The antisense oligonucleotide can further be covalently or non-covalently attached to, or associated with, a nucleotide or non-nucleotide moiety or a molecule which may include one or more of, e.g. a nucleotide, a nucleotide analog, an amino acid, a peptide, a polypeptide, a lipid moiety, a carbohydrate moiety, a marker, a matrix, any kind of beads or a tag. The antisense can be bound to the above molecules through a linker such as, but not limited to various lengths poly-A or poly-T oligonucleotide chains, polypeptide chains, aliphatic chains. In one embodiment, the linker will decrease steric interference.

The antisense oligonucleotide may further include one or more modifications, as described above.

In some embodiments, the antisense oligonucleotide sequence comprises any one of SEQ ID NO:7-12. In some embodiments, the antisense oligonucleotide sequence is set forth in any one of SEQ ID NO:7-12. In some embodiments, the antisense oligonucleotide is a salt, for example a sodium salt. In some embodiments, the antisense oligonucleotide is provided as a solution comprising a pharmaceutically acceptable carrier.

In one aspect, the invention relates to a method for reversing an oligonucleotide inhibited thrombin, the method comprising the steps of contacting the oligonucleotide inhibited thrombin with an antisense to the oligonucleotide, wherein the antisense to the oligonucleotide is immobilized on a solid phase.

Subject of the present invention is also a solid phase or support covalently bound to an antisense oligonucleotide of a thrombin-binding oligonucleotide.

The support is preferably a chromatographic material which is able to bind the antisense oligonucleotide. The chromatographic material to be employed according to the method of the invention is e.g. a hydrophilic material such as agarose, cellulose, controlled pore glass, silica gels, dextrans or ceramic material or an organic artificial polymer such as based on polyacrylamides polystyrens. Typical materials are commercially available under the trade names Agarose, Sephadex®, Sepharose®, Sephacryl® (GE, Sweden), Ultragel® (Biosepara, France), TSK-Gel, Toyopearl® (Toso Corp., Japan), HEMA (Alltech Ass. (Deerfield, Ill., USA), Eupergit® (Rohm Pharma, Darmstadt, Germany), Fractogel®, Eshmuno® (Merck Millipore, USA), Ceramic HyperD® (Pall, USA). Also materials based on azlactones (3M, St. Paul, Minn., USA) can be used.

An embodiment employs a particulate chromatographic material or a monolithic block-material. The particulate material can be suspended in an appropriate medium and the resulting slurry can be used e.g. in a chromatographic column. However, the material can be used in a batch.

In one embodiment, the antisense is bound to a support preferably via a linker, in particular a bifunctional linker, between the support and the antisense. If a bifunctional linker is used, it can be selected from the group consisting of N-hydroxy succinimide, DAPA, CNBr, epoxy, diaminodipropylamine (DADPA), 1,6 diaminohexane, succinic acid, 1,3 diamino-2-propanol, ethylendiamine (EDA), TNB, pyridyldisulfide, iodoacetamide, maleimide activated support or combinations thereof.

The support for performing the method of the invention is can be modified by a moiety which reacts with primary or secondary amino groups.

Further, a support or solid phase having the antisense covalently bound is also subject of the present invention. The support of the invention is preferably a chromatographic material, such as a hydrophilic chromatographic material such as dextran or an organic artificial polymer such as mentioned above.

The chromatographic material which forms the support may be a particulate material or a monolithic block-material. E.g, the latter is described in Hermanson et al, incorporated by reference (Hermanson G T, Mallia A K and Smith P K 1992 "Immobilization Affinity Ligand Techniques" pp. 454 Academic Press, Inc. San Diego, USA).

In another preferred embodiment of the invention the antisense is bound to the support via a linker between the support and the antisense. This is advantageous when the support does not have functional groups being capable to bind the antisense covalently. Then the support is first functionalized and then reacted with a linker which is able to bind the antisense. Spacer arms or leashes are low molecular weight molecules that are used as intermediary linkers between a support or matrix and affinity ligand such as the antisense. Preferably, the spacers comprise two functional groups on both ends for easy coupling to ligand and support. The spacer is typically a hydrocarbon compound having two functional groups at its ends. One of the two ends is attached covalently to the matrix using conventional or per se known reactions. The second end is covalently linked to the ligand using another coupling procedure.

Example of are a bifunctional linker such as N-hydroxy succinimide, DAPA, CNBr, epoxy, diaminodipropylamine (DADPA), 1,6 diaminohexane, succinic acid, 1,3 diamino-2-propanol, ethylendiamine (EDA), TNB, pyridyldisulfide, iodoacetamide, maleimide activated support or combinations thereof.

Since many functionalized supports are commercially available, it may be advantageous to start with a support which is modified by a moiety which reacts with primary or secondary amino groups.

An oligonucleotide inhibited thrombin is a thrombin combined with an oligonucleotide, said oligonucleotide can bind to thrombin in a thrombin aqueous solution, and thrombin activity is inhibited by the oligonucleotide, at least partially.

Immobilized antisense oligonucleotides to a solid phase or support are antisense oligonucleotides that are bound covalently and/or non-covalently to a solid phase or support. Examples of covalent binding antisense to a solid phase were described above. In one embodiment, the antisense is bound to the solid phase via non covalent binding. In one Example, a solid phase is covalently bound to streptavidin and the antisense oligonucleotide is covalently bound to biotin. The biotinylated antisense is non-covalently bound to streptavidin linked solid phase via biotin streptavidin affinity binding.

Different amounts (i.e. concentrations) of antisense can be bound on a support. Increase in antisense concentration on the support may accelerate reversal of inhibition resulting in an increase of thrombin activity/reactivation.

Typically, an increase of thrombin activity following inhibition with the oligonucleotide by using an antisense oligonucleotide (e.g. aptamer) is referred to re-activation of thrombin.

Re-activated thrombin, is thrombin having increased activity compared to the activity of oligonucleotide inhibited thrombin.

Re-activated thrombin can also refer to thrombin having increased activity compared to activity of thrombin after it is combined with the oligonucleotide capable of inhibiting and binding thrombin.

Using an antisense immobilized on a support (e.g. filter) with a device, container, chamber, vessel, delivery applicator, barrel, syringe etc. allows to deliver the re-activated thrombin.

The device may also include a mesh to prevent or minimize passage of the support through an opening, such as a delivery opening.

In some embodiments the device comprises at least one mesh; the mesh is configured to retain the beads within the device.

In some embodiments, the mesh size (i.e. the size of the pores therein) is at least 1.5-fold smaller (e.g. 2-fold smaller) than the size of the smallest bead. Non limiting examples of meshes are grids, etched materials, polymer networks, and the like. Meshes can be composed of any material e.g. biocompatible material such as plastic, nylon, cellulose, alloys, glass and the like. The device can comprise more than one mesh element. Filter paper is one example of a mesh—in different embodiments; other mesh structures (i.e. other than filter paper) can be used.

An oligonucleotide (e.g. aptamer) inhibited thrombin held in a container (e.g. a syringe) could be mixed with the antisense oligonucleotide (e.g. antisense of aptamer), the antisense can be bound on a solid phase or support (e.g. beads), to re-activate thrombin, at least partially, and the thrombin after re-activation can be applied (e.g. expelled from the opening of a syringe) on a desired surface. In case of using antisense oligonucleotide (e.g. antisense of aptamer) bound on a solid phase or support (e.g. beads), before application (e.g. before expelling from the opening of a syringe) the beads are separated from the mixture e.g. by filtration, precipitation over time by the gravitation force and/or following centrifugation.

For example separation/removal can be achieved by using at least one mesh e.g. positioned on the delivery opening and/or before the delivery opening.

Alternatively or in addition, the beads can be separated/removed from a liquid or from a mixture by decantation.

Typically, decantation is a process for the separation of mixtures by removing a layer of liquid, generally from which a precipitate has settled.

A precipitate can be beads bound to the antisense oligonucleotide. The antisense bound to the beads can be complexed with the oligonucleotide capable of binding thrombin.

The beads can be sedimented e.g. centrifuged by 1 min spin down at approximately 5000 g and supernatant containing the re-activated thrombin can be collected.

A "surface" is a position or location where one desires to apply the re-activated thrombin e.g. a bleeding tissue or wound on subject in need. The surface depends on the use of the re-activated thrombin. The re-activated thrombin may be used e.g. in combination with fibrinogen, for example, in hemostasis, tissue fixation, graft fixation, wound healing and anastomosis.

Provided is a delivery applicator comprising:
a barrel holding an oligonucleotide inhibited thrombin; and
a vessel having a delivery opening and holding an antisense oligonucleotide linked to a solid phase;
wherein the barrel and the vessel are capable of being in fluid communication, so that after fluid communication and contact of the inhibited thrombin with the solid phase, thrombin activity is increased/re-activated, before delivering thrombin through the delivery opening.

The barrel and vessel of the device can be in fluid communication via a resealable opening between the barrel and vessel. Provided, is a delivery applicator comprising: a container holding an oligonucleotide inhibited thrombin; and an antisense oligonucleotide linked to a solid phase, wherein the oligonucleotide inhibited thrombin and the antisense oligonucleotide are held in separate chambers that are capable of being in fluid communication, so that fluid communication between the chambers and contact between the inhibited thrombin and the solid phase results in increased thrombin, or reactivated thrombin, activity before delivery, and wherein the barrel has a re-sealable opening for delivery therethrough of the thrombin.

Increased thrombin activity is in comparison to the activity of the thrombin while being inhibited by the oligonucleotide.

In one embodiment, the chambers are divided by a septum, which is at least partially breakable, braking the septum allows mixing the oligonucleotide inhibited thrombin and the antisense oligonucleotide before administration.

In some embodiments, the container and/or chambers are flexible and breaking the septum can be achieved by applying pressure onto the container and/or chambers.

The size of each chamber and fill volumes are dependent e.g. on the intended use, suitable concentration ratios between the antisense oligonucleotides and the thrombin binding oligonucleotide, and/or desired volume.

The delivery opening of the container and/or chamber can be a Male or Female Luer Lock.

In some embodiments, the container comprises two or more chambers as described in WO1997042897A1 e.g. FIG. 19.

"Breakable" can be interchangeable with the term "peelable" and "frangible".

The term "contacting" refers to a combining action which e.g. brings the oligonucleotide inhibited thrombin into contact with the antisense in a manner that a binding interaction will occur between the antisense and the oligonucleotide and/or brings the oligonucleotide into contact with thrombin in a manner that allows a binding interaction between the thrombin and the oligonucleotide.

The term "contacting" includes the term "adding" and the term "addition".

The combining action can be for a sufficient period of time which allows contacting, binding and/or complexing e.g. between the antisense and the oligonucleotide and/or the thrombin and the oligonucleotide.

In some embodiments, the antisense is bound to the solid phase directly or indirectly.

In some embodiments, the solid phase is selected from the group consisting of chromatographic media beads and filters. Chromatographic media (beads) may include, but are not limited to cross linked agarose, cross linked dextran, methacrylic, polyvinyl, silica based materials. These may be charged and/or modified to allow covalent or non-covalent binding of antisense nucleotides. Bead grade (size) can range from superfine (20 micron mean size) and up to coarse (150 micron mean size).

Filters may include, but are not limited to, PVDF, polypropylene, nylon based. In some embodiments, the filters may have a membrane or depth construction. These may be charged and/or modified to allow covalent or non-covalent binding of antisense nucleotides. Filter porosity (rating) can range from 0.45 micron and up to about 20 micron.

"Thrombin" or "thrombin polypeptide" is a mammalian serine protease which is part of the blood coagulation cascade and converts fibrinogen into insoluble strands of fibrin, as well as catalyzes other coagulation-related reactions. In humans, prothrombin is encoded by the F2 gene, and the resulting polypeptide is proteolytically cleaved in the coagulation cascade to form thrombin. Thrombin serves, inter alia, as an active component in several hemostasis products. For example, fibrin sealants typically comprise a fibrinogen component and a thrombin component. When both components are mixed (e.g. when applied to a bleeding wound) thrombin cleaves fibrinogen and a fibrin polymer is formed.

Thrombin is a serine protease which results from the cleavage of prothrombin (Factor II), a zymogen precursor, by another serine protease (Factor Xa). Human thrombin is a 295 amino acid protein composed of two polypeptide chains joined by a disulfide bond.

The zymogen is cleaved at residue 155 and residue 271, removing the entire N-terminal 271 amino acids. An additional intramolecular cleavage by Factor Xa at residue 320 yields the active alpha thrombin molecule which is a 295 amino acid polypeptide (human) composed of a heavy and light chain held together via a single S—S bond (Krishnaswamy J, (2013) "The transition of prothrombin to thrombin". J Thromb Haemost. June; 11 Suppl 1:265-76). Thrombin, being a serine protease, can initiate its own degradation ("autolysis") by cleaving other thrombin molecules at the beta (residue 382 and 394) or gamma (residue 443 and residue 474) sites, yielding beta- and gamma-thrombin, respectively. Neither of these loops contains a classic thrombin recognition site, nor is this cleavage specific to a certain residue within the loops. Rather, these loops are both flexible and exposed and are cleaved for lack of a proper substrate and especially at high thrombin concentration (see for example, Chang, J Y. Biochem. J. (1986) 240:797-802, "The structures and proteolytic specificities of autolysed human thrombin"; Rydel T J, et al., J Biol Chem. 1994, 269(35): 22000-6. Crystallographic structure of human gamma-thrombin"; Pozzi N, et al., Biophys Chem. 2011, 159(1):6-13 "Rigidification of the autolysis loop enhances Na(+) binding to thrombin"). The inactivation of thrombin in-vivo does not proceed via this mechanism (autolysis) but rather via a specific interaction (bridged by heparin) with the serine protease inhibitor (SERPIN), anti-thrombin III (ATIII). The interaction of thrombin (and several other homologous serine proteases such as Factor X and even protein C) with ATIII is mediated via the gamma loop (see, for example, Yang, L., Blood. 2004, 104(6):1753-9, "Heparin-activated antithrombin interacts with the autolysis loop of target coagulation proteases"; and Marino, F, J Biol Chem. 2010, 285(25):19145-52. "Engineering thrombin for selective specificity toward protein C and PAR1").

Human, non-human, recombinant or non-recombinant thrombin can be used within the present invention. Thrombin is used medically e.g. as a hemostatic agent and as a component of tissue adhesives.

"Thrombin activity" is meant to include thrombin mediated conversion of heterologous substrates, including proteins e.g. fibrinogen into fibrin, as well as the conversion of Factor VIII to Factor VIIIa, XI to XIa, XIII to XIIIa, and Factor V to Va.

A "heterologous substrate" is a substrate, preferably a protein substrate, other than thrombin. In some embodiments, the thrombin activity refers to conversion of fibrinogen into fibrin.

The term "stabilizing" means, for example, maintaining the thrombin activity within the thrombin liquid solution at a level of about 70% to about 100% (e.g. about 80% to 100% or 90% to 100%) compared to the initial thrombin activity e.g. after one, 2, 3, 6, 9 and up to 12 months at room temperature and/or 2, 3, 4 weeks and up to 1 month at 37° C. and/or 3, 6, 9, 12, 18 and up to 24 months at 2-8° C. in liquid form. A thrombin solution is stable when, for example, autolytic and other protease activity is minimal or absent. The term "inhibiting thrombin activity" means, for example, preventing, partially or fully, thrombin autolysis and/or cleavage of a thrombin substrate, for example fibrinogen. In some embodiments, inhibiting thrombin activity refers to preventing or reducing thrombin autolysis in an aqueous liquid thrombin solution, so that about 60%, 65%, 70%, 75%, 80%, 85%, 90%, or preferably greater than 90% uncleaved thrombin remains in the solution.

For long-term storage, the formulation, comprising the thrombin and the thrombin binding oligonucleotide, is aliquoted into sterile vials, ampoules, or other containers, which are then sealed. In one embodiment, a seal that permits removal of the stabilized thrombin composition with a syringe through the seal is used. The container is labeled according to standard practice in the pharmaceutical or medical device field.

In some embodiments, the container is provided in a kit with a second container containing an antisense oligonucleotide. In another embodiment, the container is provided in a kit with yet a third container comprising a fibrinogen comprising component. The kit may further comprise an application device, such as a sprayer, syringe, or the like and/or a diluent and/or instructions for use.

For use, the stabilized thrombin formulation, e.g. an aqueous liquid thrombin formulation comprising a thrombin and a thrombin binding oligonucleotide, can be used directly from the container or can be further diluted to the desired concentration, generally the thrombin activity in the formulation is from about 1 IU/ml to about 15,000 IU/ml, about 20 IU/ml to 15,000 IU/ml, or 100 IU/ml to 5,000 IU/ml, 200 IU/ml to about 1000 IU/ml or about 300 IU/ml to about 1000 IU/ml, although the actual concentration will be determined by the user (e.g. medical attendant, physician, nurse, medic) i.e. according to the needs of the individual patient and on the severity of bleeding. The stabilized thrombin formulation can be applied to bleeding tissue to achieve hemostasis, per se or may be used in combination with a scaffold or matrix, for example an absorbable scaffold or matrix. The stabilized thrombin formulation can also be used as a component of tissue adhesive, fibrin sealant or fibrin glue. These and other known in the art uses of thrombin formulation are contemplated for the disclosed stabilized thrombin. Numerous uses of fibrin glue in various fields have been reported, including use as a sealant e.g. for sealing leaks, hemostatic agent/stop bleeding, adhesion prevention, to enhance healing, for joining structures, in a variety of open and laparoscopic surgeries.

Preferred hemostatic scaffolds are natural or genetically engineered absorbable polymers or synthetic absorbable polymers, or mixtures thereof. Examples of natural or genetically engineered absorbable polymers are proteins, polysaccharides and combinations thereof. Proteins include, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, polyN-glucosamine, polymannuronic acid, polyglucuronic acid, and derivatives of any of the above. Examples of synthetic absorbable polymers are aliphatic polyester polymers, copolymers, and/or combinations thereof.

As used herein, the indefinite articles "a" and "an" mean "at least one" or "one or more" unless the context clearly dictates otherwise.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate +/−10%.

A "polynucleotide coding sequence" or a sequence that "encodes" a selected polypeptide, is a nucleic acid molecule that is transcribed into DNA or RNA or transcribed and translated into a polypeptide in vivo when placed under the control of appropriate regulatory sequences (or "control elements"). The boundaries of the coding sequence are determined by a start codon at the 5' (amino) terminus and a translation stop codon at the 3' (carboxyl) terminus. A transcription termination sequence may be located 3' to the coding sequence. Typical "control elements", include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, Kozak sequences (i.e., sequences for the optimization of translation, located, for example, 5' to the coding sequence), leader sequences (heterologous or native), translation initiation codon (e.g., ATG), and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is included by an analyte, cofactor, regulatory protein, etc.), and constitutive promoters.

"Operably linked" refers to an arrangement of elements wherein the components as described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

A "recombinant" nucleic acid molecule as used herein to describe a nucleic acid molecule means a polynucleotide of genomic, cDNA, semi synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells", "host cells", "cells", "cell lines", "cell cultures", and other such terms denoting prokaryotic microorganisms or eukaryotic cell lines cultured as unicellular entities, are used interchangeably, and refer to cells which can be, or have been, used as recipients for constructs, vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

The oligonucleotides disclosed herein may be chemically synthesized or recombinantly produced. DNA and RNA oligonucleotides, including chimeras of RNA and DNA or RNA and/or DNA analogs, may be synthesized using protocols known in the art, for example as described in Caruthers et al., 1992, Methods in Enzymology 211, 3-19; PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311; Usman et al., 1987, J. Am. Chem. Soc., 109, 7845; Scaringe et al., 1990, Nucleic Acids Res., 18, 5433; all incorporated herein by reference.

In one embodiment, the oligonucleotides disclosed herein are chemically synthesized. In other embodiments, the oligonucleotides disclosed herein are produced in-vivo or ex-vivo by expression of recombinant DNA in prokaryotic or eukaryotic host cells to generate DNA and/or RNA oligonucleotides. In various embodiments, provided is a recombinant peptide encoded by an isolated nucleic acid sequence. In some embodiments, the thrombin binding oligonucleotide comprises a nucleic acid sequence set forth in any one of SEQ ID NOS: 1 to 6. In some embodiments, the antisense oligonucleotide comprises a nucleic acid sequence set forth in any one of SEQ ID NOS: 7 to 12. Accordingly, provided herein is a vector comprising the nucleic acid sequence used to generate a DNA or RNA oligonucleotide, operatively linked to a promoter element. Further provided is a host cell comprising such vector.

As used herein, an oligonucleotide or aptamer is said to "interact" with or "bind" to a protein (e.g. thrombin binding oligonucleotide with thrombin) if it associates with protein preferably via non-covalent binding forces, for example van der Waals and electrostatic forces.

"Room temperature" is meant to include temperature of about 20° C. to about 28° C., or 22° C. to about 26° C.

As used herein the terms "autolysis" or "auto degradation" refer to the unfavorable molecular degradation of thrombin into an inactive or partially active form.

A preferred thrombin binding oligonucleotide as disclosed herein, is capable of reversibly inhibiting thrombin activity, for example, by reducing thrombin autolysis and thrombin activity towards fibrinogen wherein the inhibition is reversible with an antisense oligonucleotide. Without wishing to be bound to theory, the antisense oligonucleotide has stronger binding affinity to the thrombin binding oligonucleotide than thrombin to the thrombin binding oligonucleotide.

The term "affinity" refers to the strength of binding and can be expressed quantitatively as a dissociation constant (Kd).

In one embodiment, the thrombin binding oligonucleotide interacts with the antisense oligonucleotide disclosed herein with at least 1.10, 1.15, 1.20, 1.25, 1.30, 1.35, 1.40, 1.45, 1.50, 1.55, 2 fold greater affinity, more preferably at least 5 fold greater affinity and even more preferably at least 10, fold greater affinity than it interacts with thrombin. Binding affinity (i.e., Kd) can be determined using standard techniques.

The term "an effective amount" refers to the amount of an antisense oligonucleotide disclosed herein required to bind the thrombin binding oligonucleotide and reverse the inhibition of thrombin activity.

The "pharmaceutically acceptable" or "pharmacologically acceptable" carriers, solvents, diluents, excipients, and vehicles generally refer to inert, non-toxic solid or liquid fillers, diluents or encapsulating material not reacting with the active ingredients of the compositions disclosed herein. Acceptable excipients include, without limitation, saline; acetic acid or acetate; calcium, sodium and chloride ions; mannitol; albumin; or combination thereof.

The invention provides oligonucleotides useful in practicing the present invention.

Provided herein are compounds and methods for stabilization of thrombin activity in liquid thrombin formulations, wherein stabilizing the thrombin activity refers, for example, to reducing or preventing autolytic and biological activity. Details of the exemplary oligonucleotides useful in practicing the invention, are provided in Example 1, hereinbelow and in the sequence listing, incorporated herewith.

Provided herein are methods of screening for oligonucleotides capable of reversibly stabilizing thrombin activity. Accordingly, provided is a method for screening for an oligonucleotide capable of inhibiting and thereby stabilizing the activity of thrombin in a liquid thrombin formulation, comprising
  a. contacting thrombin or a fragment thereof, each exhibiting an initial activity of 4 to 15,000 IU/ml, with a set of test thrombin binding oligonucleotides and identifying one or more thrombin binding oligonucleotides which inhibit, at least partially, the initial activity; and
  b. contacting the thrombin bound oligonucleotide of step a) with a set of test antisense oligonucleotides;
whereby restoration of at least 4 IU/ml thrombin activity by an oligonucleotide antisense following step (b) indicates: 1) a potential thrombin binding oligonucleotide for thrombin stabilization; and 2) a potential antisense oligonucleotide to reverse the inhibitory effect of the thrombin binding oligonucleotide.

In some embodiments of the screening method, the thrombin has an initial activity of 4 to 15,000 IU/ml, about 20 IU/ml to 15,000 IU/ml, or 100 IU/ml to 5,000 IU/ml, 200 IU/ml to about 1000 IU/ml or about 300 IU/ml to about 1000 IU/ml.

In some embodiments the antisense oligonucleotide restores thrombin activity to at least 4 IU/ml, at least about 20 IU/ml, at least about 100 IU/ml or at least about 300 IU/ml, at least about 1000 IU/ml and up to 1500 IU/ml of the initial activity of thrombin.

Alternatively, provided is a method for screening for an oligonucleotide capable of inhibiting and thereby stabilizing the activity of thrombin in an aqueous liquid thrombin formulation, comprising
  a. contacting thrombin or a fragment thereof, each exhibiting an initial activity, with a set of test thrombin binding oligonucleotides and identifying one or more thrombin binding oligonucleotides which inhibit at least 60% of the initial activity; and
  b. contacting a thrombin bound oligonucleotide of step a) with a set of test antisense oligonucleotides;

whereby restoration of more than 40% of the initial activity by an oligonucleotide antisense following step (b) indicates: 1) a potential thrombin binding oligonucleotide for thrombin stabilization; and 2) a potential antisense oligonucleotide to reverse the inhibitory effect of the thrombin binding oligonucleotide.

In some embodiments of the method, the one or more thrombin binding oligonucleotides inhibit, at least 60% of the initial activity of thrombin, at least 70%, at least 75%, at least 80%, at least 85% or at least 90% of the initial thrombin activity.

In some embodiments of the method the antisense oligonucleotide restores at least, 40%, 50%, 60%, 70% and up to 100% of the initial activity of thrombin.

In some embodiments, the methods further include the step of isolating the one or more test thrombin binding oligonucleotides and/or of testing the one or more test antisense oligonucleotides its ability to inhibit and stabilize thrombin activity.

In some embodiments of the methods, the set of test thrombin binding oligonucleotides includes one or more test thrombin binding oligonucleotides and the set of test antisense oligonucleotides includes one or more test antisense oligonucleotides.

The fibrinogen can be prepared from initial blood composition. The blood composition can be whole blood or blood fractions, i.e. a product of whole blood such as plasma. Fibrinogen can be autologous, human including pooled plasma, or of non-human source. It is also possible that the fibrinogen is prepared by recombinant methods or can be chemically modified.

In one embodiment of the invention, the fibrinogen solution is comprised from a biologically active component (BAC) which is a solution of proteins derived from blood plasma which can further comprise anti fibrinolytic agents such as tranexamic acid and/or stabilizers such as arginine, lysine, their pharmaceutically acceptable salts, or mixtures thereof. BAC can be derived from cryoprecipitate, in particular concentrated cryoprecipitate.

The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitate that contains fibrinogen and factor XIII. The precipitate can be collected, for example by centrifugation and dissolved in a suitable buffer such as a buffer containing 120 mM sodium chloride, 10 mM trisodium citrate, 120 mM glycine, 95 mM arginine hydrochloride. The solution of BAC can comprise additional factors such as for example factor VIII, fibronectin, von Willebrand factor (vWF), vitronectin, etc. for example as described in U.S. Pat. No. 6,121,232 and WO9833533. The composition of BAC can comprise stabilizers such as tranexamic acid and arginine hydrochloride. The amount of tranexamic acid in the solution of BAC can be from about 80 to about 110 mg/ml.

In another embodiment, the concentration of plasminogen and plasmin in the BAC composition is lowered to equal or less than 15 µg/ml like for example 5 µg/ml or less plasminogen e.g. using a method as described in U.S. Pat. No. 7,125,569, EP 1,390,485 and WO02095019. In another embodiment of the invention, when the concentration of plasminogen and plasmin in the BAC composition is lowered, the composition does not contain tranexamic acid or aprotinin.

The fibrinogen solution may be the BAC2 component (from EVICEL®) or any other fibrinogen containing solution, such as purified recombinant fibrinogen or cryoprecipitate produced from human plasma.

While the following examples demonstrate certain embodiments of the invention, they are not to be interpreted as limiting the scope of the invention, but rather as contributing to a complete description of the invention.

EXAMPLES

Example 1

Thrombin Binding Oligonucleotides

Exemplary thrombin binding oligonucleotides were identified in Bock et al., Nature. 1992. 355(6360):564-6 and Tasset and Kubik, 1997, J Mol Biol. 272(5):688-98. For simplicity, these oligonucleotides were designated herein as Thrombin Binding Aptamer 1 and 2 (TBA1 (Bock, 1992), TBA2 (Tasset, 1997)), respectively. TBA1, BOCK-15, which binds to EXOSITE 1 of thrombin has a nucleic acid sequence set forth in SEQ ID NO:1 5'-GGTTGGTGTGGTTGG or an extension of SEQ ID NO:1 set forth in SEQ ID NO:2 5'-GGGTTGGGTGTGGGTTGGG. TBA2, TASSET-29, which binds to EXOSITE II thrombin has a nucleic acid sequence set forth in SEQ ID NO:3 5'-AGTCCGTGGTAGGGCAGGTTGGGGTGACT. RNA counterparts of the thrombin binding oligonucleotides are set forth in SEQ ID NOS:4-6.

The thrombin binding aptamers have a short half-life in the blood (Dougan, et al., Nucl Med Biol. 2000. 27(3):289-97) and at least TBA1 has been shown to be safe (DeAnda et al., Ann Thorac Surg. 1994. 58(2):344-50).

Exemplary thrombin binding oligonucleotides and antisense oligonucleotides disclosed herein are provided in the appended sequence listing Example 2

Stabilization of Thrombin Activity

Aqueous liquid thrombin, in its purified and concentrated form 1000 international units [IU]/ml and about 0.3 mg/ml thrombin, rapidly undergoes autolysis at room temperature (RT) causing a significant loss of activity. Therefore, aqueous liquid thrombin activity is reduced when incubated at room temperature for prolonged periods of time (e.g. after 72 to 144 hours) inter alia, due to autolytic degradation. The decrease of thrombin stability in aqueous liquid solution can be assessed by measuring thrombin activity after prolonged periods of time under permissive temperature (e.g. RT or 37° C.).

Thrombin activity—clotting assay: Briefly, a thrombin standard curve was created using between 4-10 International Units (IU)/ml using an in house validated standard solution. Higher concentrations of thrombin resulted in unmeasurably fast fibrin clotting times and therefore, respective thrombin concentrations were extrapolated from the standard curve.

Clotting time was assessed by adding 40 µl thrombin to 160 µl of a 0.1% purified commercial fibrinogen solution in a test cuvette. The time to clot was assayed in an automated clotting machine (Stat4, Stago Diagnostica). The machine generates an oscillating electromagnetic field which moves a small metal ball inside the cuvette. Clotting was determined to have occurred when the ball movement stopped. Thrombin concentration in test samples was extrapolated from the clotting times against the standard curve.

The physical properties of fibrin clots were tested by measuring Young's Modulus (in kPa) using a Lloyd Instruments LFplus machine. Briefly, 8 IU/ml thrombin were incubated in a cast mold with an equivalent volume of a 7% fibrinogen containing solution (BAC2), yielding 4 IU/ml and 3.5% concentrations of thrombin and fibrinogen, respectively, for 30 minutes at 37° C. After 30 minutes, the clot was placed in the machine and subjected to pulling at increasing force. The slope of the stretching of the clot as a function of the pulling force (Young's Modulus) was extrapolated.

Thrombin activity to form fibrin sealant—drop test assay: In this assay, one barrel of a two-component fibrin sealant device, was filled with a specified amount of thrombin (typically 200 IU/ml thrombin [~2 μM]) and the second barrel was filled with standard BAC2-fibrinogen solution (~7% fibrinogen). The device was placed above a tilted plane (~15-30°) on which millimeter paper was placed. A mechanized lever pushed both barrels simultaneously, expressing equal and measured amounts of both solutions through a conjoined tip. The drop containing the mix of the two components trickled down the slope until a clot formed. The distance traveled by the drop was measured, being a function of the rate of fibrinogen polymerization and, thereby of the effective concentration of thrombin used.

Reversible inhibition of thrombin activity by TBA. TBA1 was shown to reversibly inhibit thrombin activity in a dose-dependent manner. A stock solution of 10 IU/ml thrombin which is approximately equivalent to 0.1 μM was prepared. TBA1 at increasing concentrations ranging from equimolar amount (0.1 μM) and up to 10-fold higher (1 μM) was added to the thrombin, resulting in dose-dependent inhibition of thrombin activity (FIG. 1, dotted line). The concept of reversible inhibition of thrombin relies on the possibility of an antisense oligonucleotide to effectively counteract TBA1 inhibition of thrombin. Antisense oligonucleotides (AS) SEQ ID No: 7 to TBA1 SEQ ID NO: 1—were added at equimolar amounts to the TBA1, and allowed to incubate for 5-30 minutes. This solution was used in the thrombin activity assay in order to assess the efficiency of the antisense neutralization of TBA1. Indeed, the neutralization was efficient as is evident by the fact that the extrapolated activity from this assay remained 10 IU/ml (solid line in FIG. 1). In FIG. 1, the x-axis is concentration of TBA1 and antisense in micromoles. Taken together, antisense oligonucleotides effectively counter the TBA1 induced inhibition of thrombin and TBA1 inhibits 10 IU/ml (~0.1 μM) thrombin in a dose dependent manner. Equimolar antisense completely restores activity.

Example 3

Activity of Thrombin with Thrombin Binding Oligonucleotide and Antisense Oligonucleotide Samples of 1000 IU/ml purified thrombin were stabilized with increasing final concentrations of TBA1 (SEQ ID NO: 1) from 1 μM and up to 40 μM (using a volume ratio of 1:10 TBA1:thrombin). The final thrombin concentration in the mixed samples was 9 μM. The samples were incubated for up to 90 days at room temperature (RT) [FIG. 2A] or 180 days at 2-8° C. [FIG. 2C].

Samples of 1000 IU/ml purified thrombin were stabilized with increasing final concentrations of TBA1 (SEQ ID NO: 1) from 1 μM and up to 25 μM (using a volume ratio of 1:10 TBA1:thrombin). The final thrombin concentration in the mixed samples was 9 μM. The samples were incubated for up 14 days at 37° C. [FIG. 2B].

In order to assess the activity of the inhibited thrombin, the thrombin/TBA1 mix was incubated with an antisense oligonucleotide (SEQ ID NO:7) at equivalent concentrations to TBA1 for 30 minutes. The samples were then diluted 100-fold for testing within the range of the thrombin clotting assay (4-10 IU/ml) in the test buffer, and assayed for activity as before.

Figure 2A:
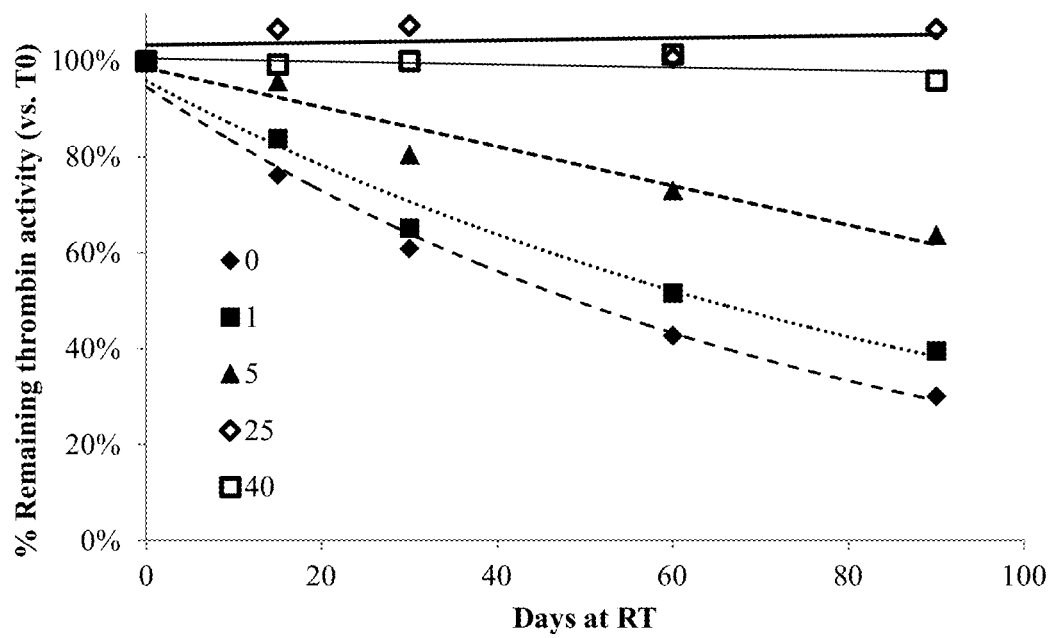
Figure 2B:
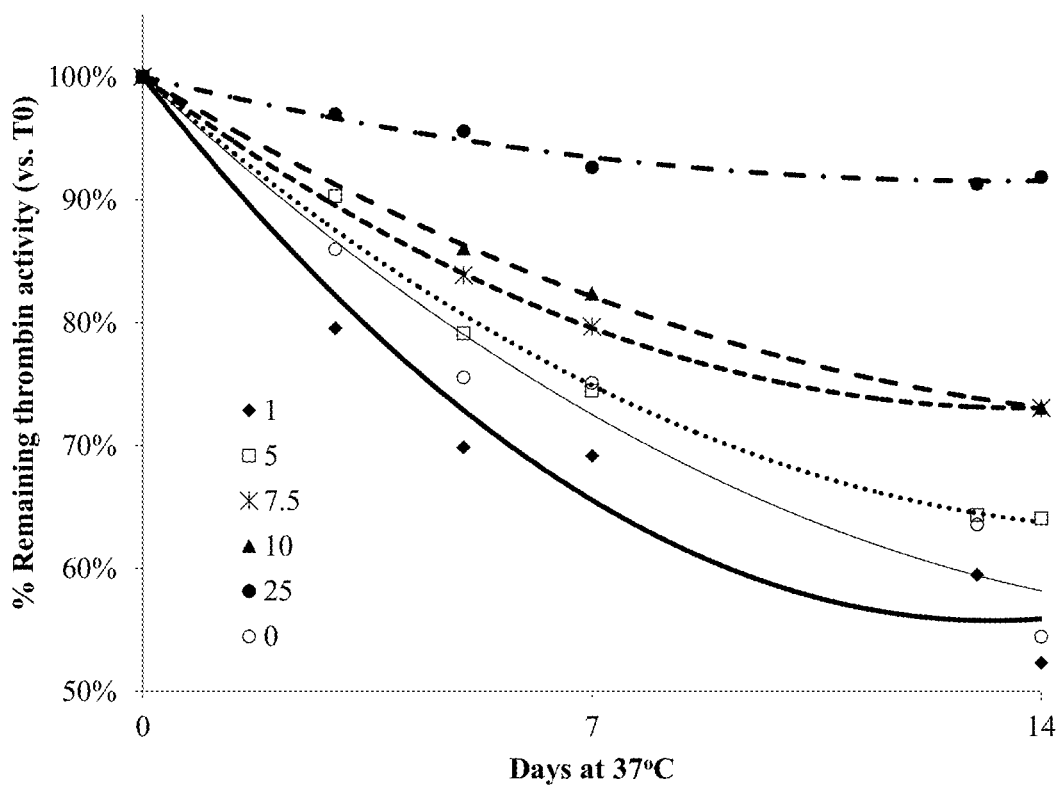
Figure 2C:
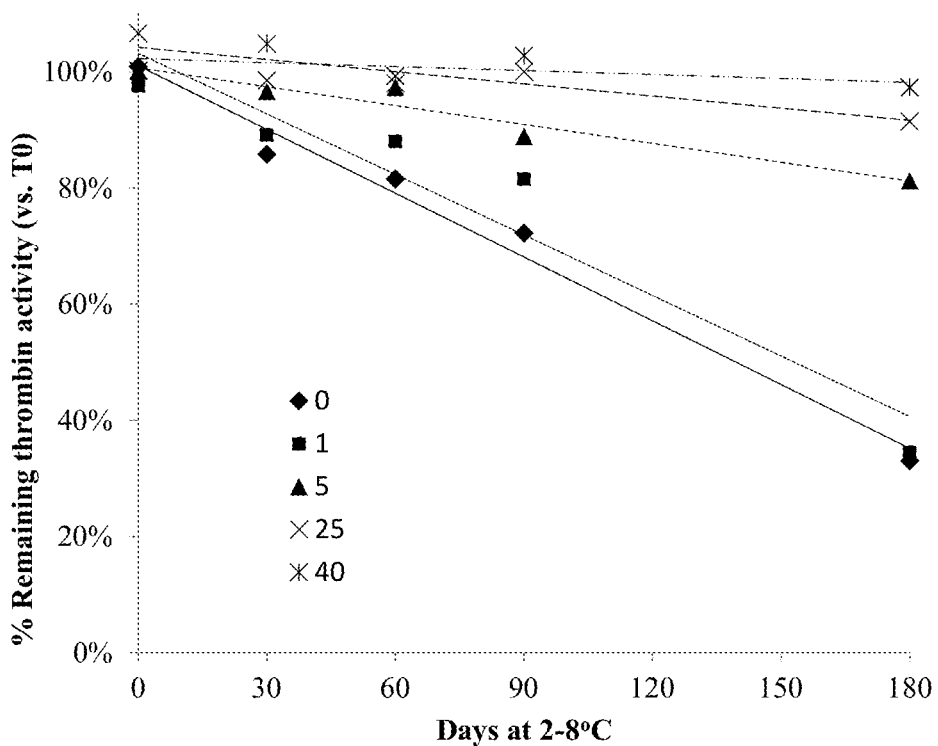

FIGS. 2A-2D show that TBA1 clearly stabilized thrombin in a dose-dependent manner. FIGS. 2A, 2B and 2C show percent thrombin remaining when TBA1 was added to purified thrombin (as in the thrombin component of EVICEL® Fibrin sealant, ~1000 IU/ml) at the indicated concentrations and incubated at RT for up to 90 days (FIG. 2A) at 37° C. for up to 14 days (FIG. 2B) and at 2-8° C. for 180 days (FIG. 2C).

At RT, addition of 25 to 40 μM TBA1 fully stabilized thrombin activity for 3 months (FIG. 2A). At 37° C. less than 10% activity were lost after 14 days at the presence of 25 μM TBA1 (FIG. 2B).

At 2-8° C., close to 100% thrombin activity were retained with 40 μM TBA1 after 180 days (FIG. 2C).

Figure 2D:
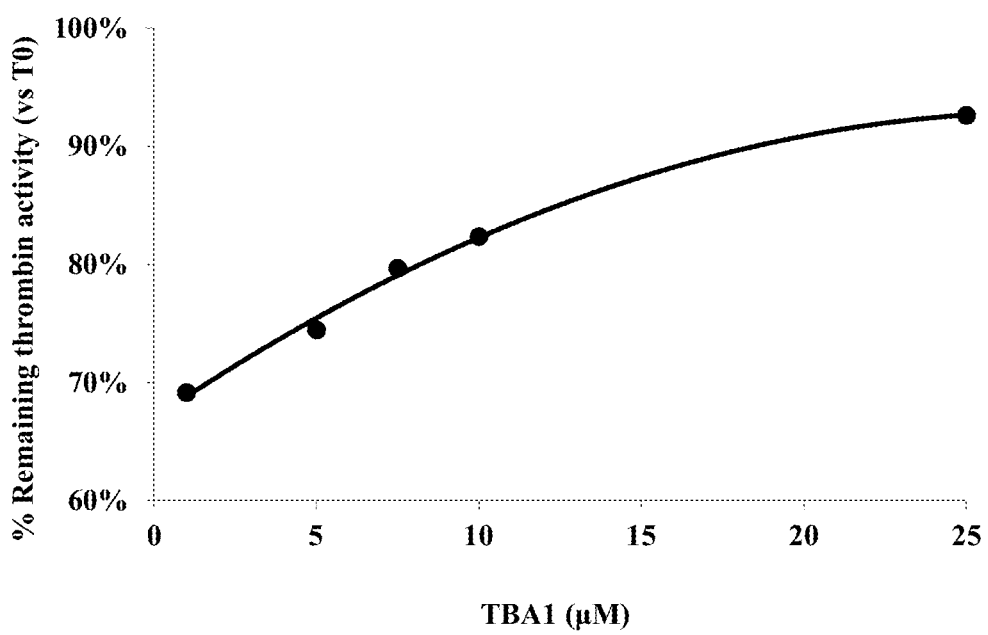

Remaining thrombin activities after incubation at 37° C. for 7 days in the presence of different TBA1 concentrations as in FIG. 2B are plotted against the TBA1 concentrations (FIG. 2D). Thus, thrombin stabilization by TBA1 is correlated with TBA1 concentration and therefore with thrombin inhibition. These data thus show that TBA1 stabilizes thrombin by virtue of inhibition of its autocatalytic activity.

Example 4

Physical Properties of Clot Prepared with Thrombin Containing TBA and Antisense Oligonucleotide The physical properties of a clot formed with thrombin containing TBA and antisense oligonucleotide were assessed. 8 IU/ml (about 0.08 μM) thrombin were incubated with 25 μM of TBA1 and 25 μM of antisense oligonucleotide. After clot formation was initiated by mixing the thrombin with a 7% fibrinogen containing solution (BAC2), and 30 minutes incubation, elasticity of the resulting clot was tested.

Figure 3:
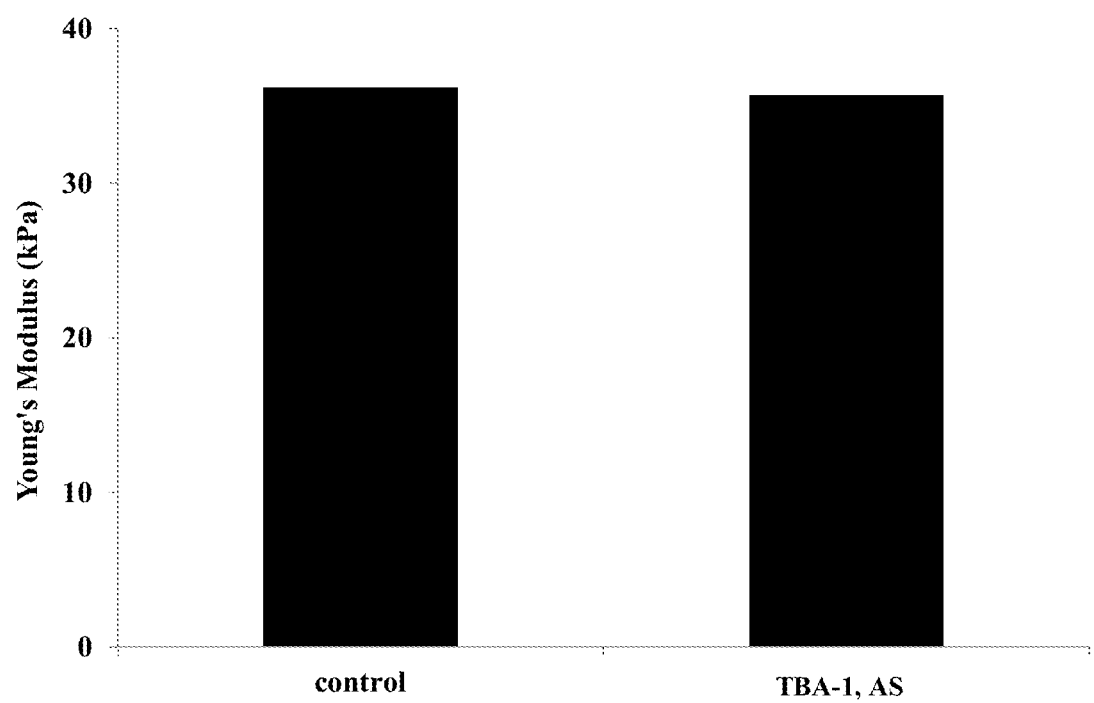

The results (FIG. 3) show that the presence of TBA1 and the antisense oligonucleotide does not change the elasticity of the clot, one of its most important physical properties.

Example 5

Effect of Antisense Oligonucleotide on the Rate of Inhibition Reversibility

The rate at which the antisense oligonucleotide reverses the inhibitory effect of TBA1 was assessed. To this end, thrombin was diluted to 10 IU/ml (~0.1 μM) for the thrombin activity assay and TBA1 was added at 5, or 25 μM (resulting in 50:1 or 250:1 TBA1:thrombin ratio, respectively). All concentrations are final concentrations within the thrombin sample. The thrombin activity assay was initiated by adding a fibrinogen component including an equimolar amount of the antisense oligonucleotides.

Four (4) volumes of fibrinogen solution containing AS were added to one volume of thrombin solution, so that the final TBA1 concentration in the 5 and 25 uM TBA1-containing thrombin solutions was, 1 and 5 μM, respectively, and thrombin was at 2 IU/ml (or ~0.02 μM). The TBA1/thrombin ratios remained unchanged. In order to assess potential inhibitory effect of the antisense oligonucleotides, a control containing antisense alone (without TBA1) was included.

Thrombin activity in this assay was measured as the time required for thrombin to clot the fibrinogen. Thus, 100% extrapolated activity would indicate that TBA1 inhibition was neutralized by the antisense oligonucleotides at a time constant which is faster than the sensitivity of the assay ($1/10^{th}$ of a second). Antisense oligonucleotides were added at a range between $1/10^{th}$ and 8-fold that of the TBA1, in order to overcome the possibly too slow binding rate between the two components. As can be seen in FIG. 4, at TBA1 final concentration 1 µM (4A) as well as, 5 µM (4B), there was a delay in the clotting reaction, even when the antisense oligonucleotide was added to the fibrinogen solution at large excess compared to TBA. Taken together, apparently the short time available for TBA1 neutralization with the antisense oligonucleotide when added in the fibrinogen component is not long enough to efficiently neutralize the TBA-1 mediated inhibition of thrombin.

The molar ratio between TBA1:thrombin did also appear to have an effect on the reaction (50:1 or 250:1 TBA1:thrombin ratio resulted in recovery 70% and 60%, respectively). While addition of an antisense excess of 5:1 (antisense:TBA1) seemed to enhance the rate of TBA1 neutralization in the reaction performed at lower TBA1 concentrations (5 µM antisense:1 µM TBA1, FIG. 4A), a 4:1 or 8:1 excess did not elicit a higher recovery of thrombin activity when the assay was performed at higher TBA1 concentrations (20 and 40 µM antisense:5 µM TBA1, respectively, FIG. 4B). Finally, antisense oligonucleotide added to thrombin without TBA1 also caused a small but detectable reduction in the thrombin activity (FIGS. 4A and B).

Example 6

Incomplete Reversal of Large Excess TBA-Inhibited Thrombin Activity with Antisense Oligonucleotides The data depicted in FIG. 1 showed that thrombin inhibition by TBA is fully reversible. Rapid reversal is a key attribute for any reversible inhibitor to be used in a fibrin sealant mixture.

To test the time needed for complete reversal of thrombin inhibition by TBA1, we examined the actual time required for efficient reversal of TBA1 added in excess. 25 µM of TBA1 were added to 10 IU/ml (0.1 µM) of thrombin, a concentration that can be directly tested in the thrombin activity assay. This represents a 250:1 TBA1:thrombin ratio. Antisense oligonucleotide was added at an equimolar amount to TBA1 (25 µM) at time 0, and samples were tested using the thrombin clotting assay at various time points thereafter (the thrombin:TBA1:antisense mixture was diluted together in the reaction cuvette so that the molar ratio between them does not change). This assay was also performed for TBA2 with a corresponding antisense oligonucleotide. The results showed that while thrombin activity measured after 60 seconds is approximately 7 IU/ml (aprox. 70%), there was no improvement after 600 seconds, and activity did not fully recover after 1800 seconds (FIG. 5). Countering TBA2 with antisense was even less efficient (FIG. 5). Surprisingly, a large excess of TBA over thrombin cannot be efficiently neutralized with antisense oligonucleotide, even after long incubations.

Example 7

Drop Test with TBA1

Without wishing to be bound to theory, two factors may contribute to the rate of the removal of inhibition by TBA1 from thrombin by antisense oligonucleotide: the absolute concentration of the TBA, and the molar ratio between TBA and thrombin. The effect of increasing the concentration of thrombin, while maintaining TBA1 in the effective stabilization range (~5-25 µM), thus changing the molar ratio between thrombin and TBA1, was tested. The thrombin clotting assay cannot be performed at thrombin concentrations used in fibrin sealants, as clotting is too rapid to be measured. Therefore, the drop test assay, which is performed with 200 IU/ml thrombin (~2 µM) was utilized. This assay is also, essentially, a kinetic assay. Non-polymerized fibrinogen is liquid and slides down a tilted slope, and the rate of fibrinogen polymerization induced by thrombin determines the time required for the mixture to clot and, consequently, to stop moving. This assay was performed in two ways. First, TBA1 was added to the thrombin component and antisense oligonucleotides to the fibrinogen (BAC2) component. The interaction time afforded to the two components is very short: from the moment that both mixtures are expressed from the common tip and until the mixture is polymerized. Under these conditions, TBA1 was not rapidly enough neutralized by the antisense oligonucleotide, and the distance traversed by the mixture was almost double that of control. Doubling the antisense concentration did not improve the rate of interaction (see FIG. 6, control without TBA1, left bar vs. $2^{nd}$ and $3^{rd}$ bar). In the second set of experiments, TBA1 was added to the thrombin component, and subsequently the antisense oligonucleotide was added and pre-incubated for several minutes (5-30). Here, the molar ratios between TBA1 and thrombin were critical. At the 12.5:1 molar ratio (25 µM TBA1:~2 µM thrombin), there was a clear reduction of the distance travelled by the clot as compared to the previous test (FIG. 6, compare the $2^{nd}$ and $3^{rd}$ bars to the $5^{th}$ bar). Surprisingly, upon reduction of the TBA1:thrombin molar ratio to that effectively used in the thrombin stabilization experiments (FIG. 2), 2.5:1 (5 µM TBA1:~2 µM thrombin), no significant difference from control was observed (FIG. 6, $1^{st}$ vs. $4^{th}$ bar).

These results demonstrated that the TBA1:thrombin ratio affects the reversibility of TBA1 inhibition by the antisense oligonucleotide.

In a modified drop test 1000 IU/ml thrombin, was effectively stabilized by 25 µM TBA1 (FIG. 2). Rapid neutralization of TBA1 is a requirement from a fibrin sealant. To test this under real-life settings, the drop test assay was modified to include undiluted thrombin (1000 IU/ml) with 25 µM TBA1. Antisense oligonucleotide was added to the thrombin/TBA1 compartment just prior to the start of the test. This significantly delayed clot formation (FIG. 7) as compared to control, uninhibited thrombin. The same test was repeated, but with two minutes incubation of the antisense with thrombin/TBA1 prior to drop test start. No significant differences were now seen compared to control (FIG. 7).

Taken together, when TBA1 was used with thrombin, at concentrations efficiently stabilizing thrombin, antisense was efficient in counteracting thrombin inhibition, provided it was added to thrombin ~2 minutes prior to testing of the sealant, a time frame acceptable for practical clinical use.

The drop test results, using actual drug product concentrations of thrombin, and TBA1 concentrations shown to efficiently stabilize thrombin activity, indicated that the few minutes required to prepare the formulation for use are sufficient to allow effective neutralization of TBA1 with antisense oligonucleotide.

Example 8

Preclinical Testing of Reversibly Stabilized Thrombin

To assess the use of the disclosed formulations in a preclinical setting, the capability of stabilized EVICEL® (a typical fibrin sealant) to stop bleeding in the heparinized rat kidney model was assessed (Macromol Biosci. 2010 Jan. 11; 10 (1):33-9. doi: 10.1002/mabi.200900129. Hemostatic efficacy of biological self-assembling peptide nanofibers in a rat kidney model. Song H1, Zhang L, Zhao X.). In this model, a kidney was transected out of an anaesthetized rat and the main artery clamped. A transversal cut was performed through the entire cross-section of the kidney and fibrin sealant applied. The clamp was then released and the efficiency of the hemostatic composition assessed by the amount of blood lost through the kidney surface. In order to prevent endogenous hemostasis, the rats were pre-injected with 300 IU/kg body weight of heparin. EVICEL® (FIG. 8, control) vs. EVICEL® in which the thrombin component was inhibited with 25 μM of TBA1, and then contacted with the same amount of antisense oligonucleotide just prior to application (FIG. 8, test) were tested. The time elapsed between applying the antisense oligonucleotides and the actual spraying of the fibrin sealant (the time required to assemble the EVICEL® two component double barreled syringe, and spray tip) is approximately 2 minutes. As can be seen in FIG. 8, the test group was at least as efficient as the control group in achieving hemostasis.

Example 9

Reversal of TBA-Inhibited Thrombin Activity with Streptavidin-Sepharose-Immobilized Biotinylated Antisense Oligonucleotides To examine reversal of the thrombin inhibitory effect of TBA1 by immobilized antisense oligonucleotides, a 5' biotinylated (Btn) derivative of antisense TBA1 (AS) was synthesized ([Btn]AS). Streptavidin-Sepharose resin was prepared according to manufacturer instructions (GE product code 17-5113-01; having a binding capacity which is biotin >300 nmol/ml medium). Briefly, 100 nmol [Btn]AS was set to bind to 1 ml settled Streptavidin-Sepharose beads (Mean particle size 34 μm), representing a minimum of 3 fold excess of streptavidin to biotin over the [Btn]AS, for 15 minutes at ambient temperature. Binding reaction was carried out according to manufacturer instructions in reaction buffer: 20 mM sodium phosphate, 0.15 M NaCl, pH 7.5. A complex Sepharose-Streptavidin/[Btn]AS was formed (Beads-[Btn]AS). The complex was sedimented by 1 min spin down at approximately 5000 g, supernatant decanted. Washing was carried out three times (in reaction buffer). The Beads-[Btn]AS complex was resuspended with reaction buffer to 5% (v/v) slurry.

To establish a base-line for the experiment, 10 μl of 1000 IU/ml Thrombin-were mixed with 0, 0.1, 0.2, 0.5 and 1 μM TBA1 in a final volume of 1 ml. The mixture was incubated for 30 min at ambient temperature and thrombin activity was determined to be 10.99 and 2.38 IU/ml with 0 or 1 μM TBA1, respectively (FIG. 9A). To determine the extent of the reversal inhibition, equimolar amounts of antisense in {[Btn]AS} or {Beads-[Btn]AS} were added to pre-incubated base-line mixtures of thrombin and TBA1, thrombin activity was assayed after 15 min incubation at ambient temperature. Reversal of inhibition of TBA1 by {[Btn]AS} or {Beads-[Btn]AS} was equal and incomplete (FIG. 9A)—thrombin activity increased from 6.71 IU/ml (without AS) to 9.08 IU/ml or 8.84 IU/ml for 0.1 μM TBA1/AS instead of 10.71 IU/ml without TBA1 (FIG. 1) and increased from 2.38 IU/ml (without AS) to 5.9 IU/ml or 5.76 IU/ml for 1 μM TBA1/AS instead of 10.26 IU/ml without TBA1 (FIG. 1). FIG. 1 was used as a reference for the inhibition level of TBA1+AS.

Without being bound by the mechanism, complete reversal of inhibition was not obtained, most likely because of steric hindrance. Addition of a linker sequence may allow optimal binding of antisense nucleotide to TBA1.

To test possible artifacts of beads alone on thrombin activity, 200 microliter of beads (5% slurry) and 10 μl of thrombin 1000 IU/ml were mixed with thrombin dilution buffer (0.4% sodium citrate di-hydrate, 0.9% NaCl, 1% BSA) to a final volume of 1 ml. Thrombin activity assayed after 30 min incubation at ambient temperature was 10.99 IU/ml.

To test possible artifacts of [Btn]AS on thrombin activity, 50 microliter of [Btn]AS (20 μM) and 10 μl of thrombin 1000 IU/ml were mixed with thrombin dilution buffer to a final volume of 1 ml. Thrombin activity assayed after 30 min incubation at ambient temperature was 10.58 IU/ml.

To test possible artifacts of Beads-[Btn]AS on thrombin activity, 200 microliter of Beads-[Btn]AS (5% slurry) and 10 μl of thrombin 1000 IU/ml were mixed with thrombin dilution buffer to a final volume of 1 ml. Thrombin activity assayed after 30 min incubation at ambient temperature was 10.34 IU/ml.

The results show that beads, Beads-[Btn]AS and [Btn]AS do not affect thrombin activity.

To establish kinetics of reversal of inhibitory effect of TBA1 equimolar amounts of Beads-[Btn]AS were added to pre-incubated base-line mixtures after 2, 5, 10 and 15 min. The mixtures were tested immediately, after the addition of AS, for thrombin activity. Maximal reversal of inhibition was observed after 10 and 15 min for 0.1 or 0.2 and 0.5 or 1 μM TBA1, respectively (FIG. 9B). Thrombin inhibition and re-activation timing can be optimized as needed, depending on the intended use.

The data gathered from the above described experiments show that thrombin binding oligonucleotides (e.g. aptamers) function as efficient stabilizers of highly concentrated, purified thrombin in liquid formulation. Their concentration preferably falls within a defined range of molar ratios compared to the thrombin. The reversal of TBAs is possible and efficient, provided that the molar ratio of TBA:thrombin does not exceed 10:1, and is preferably about 2.5:1 to about 4:1. The amount of antisense oligonucleotides used to counter the TBA preferably does not exceed the amount of TBA by more than ~20% so that free antisense oligonucleotide concentration does not exceed ~5 μM which is shown here to also inhibit thrombin activity on fibrinogen in a clotting assay. Under these conditions, the time required for efficient countering TBA is <2 minutes, which is approximately the time required in the clinic/surgery to assemble and position the device for application. Thus, this invention represents an applicable means to efficiently stabilize highly purified thrombin in the liquid formulation, in a reversible manner, with no expected toxicity or immunogenicity.

Although various embodiments have been described herein, many modifications and variations to those embodiments may be implemented. Also, where materials are disclosed for certain components, other materials may be used. The foregoing description and following claims are intended to cover all such modification and variations.

The disclosure of applications, patents and publications, cited above is hereby incorporated by reference.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Citation or identification of any reference in this application shall not be construed as an admission that such reference is available as prior art to the invention.

Section headings are used herein to ease understanding of the specification and should not be construed as necessarily limiting.

The invention claimed is:

1. A formulation for conversion of fibrinogen to fibrin comprising: a thrombin solution comprising thrombin binding oligonucleotide having a molar ratio in the range of 9:1 to about 1:1 thrombin binding oligonucleotide:thrombin, wherein the thrombin concentration is equal to or higher than 4 IU/ml-15,000 IU/ml, and wherein the thrombin binding oligonucleotide is an aptamer of about 14 to about 60 nucleotides in length comprising a nucleic acid sequence selected from SEQ ID NO: 1 to SEQ ID NO: 6.

2. The formulation of claim 1, wherein the thrombin concentration is 20 IU/ml-15,000 IU/ml.

3. The formulation of claim 1, wherein the formulation is a component of a fibrin sealant.

4. The formulation of claim 1, further comprising an antisense nucleotide, wherein the dissociation constant (Kd) between the thrombin binding oligonucleotide and the antisense oligonucleotide is less than 0.2 μM (microM).

5. The formulation of claim 1, wherein the thrombin binding oligonucleotide binds to exosite I of thrombin.

6. The formulation of claim 1, wherein the nucleic acid sequence is set forth in SEQ ID NO: 1.

* * * * *

```
                        SEQUENCE LISTING

<160> NUMBER OF SEQ ID NOS: 12

<210> SEQ ID NO 1
<211> LENGTH: 15
<212> TYPE: DNA
<213> ORGANISM: Artificial Sequence
<220> FEATURE:
<223> OTHER INFORMATION: thrombin binding oligonucleotide

<400> SEQUENCE: 1
ggttggtgtg gttgg                                                    15

<210> SEQ ID NO 2
<211> LENGTH: 19
<212> TYPE: DNA
<213> ORGANISM: ARTIFICIAL
<220> FEATURE:
<223> OTHER INFORMATION: thrombin binding oligonucleotide

<400> SEQUENCE: 2
gggttgggtg tgggttggg                                                19

<210> SEQ ID NO 3
<211> LENGTH: 29
<212> TYPE: DNA
<213> ORGANISM: ARTIFICIAL
<220> FEATURE:
<223> OTHER INFORMATION: thrombin binding oligonucleotide

<400> SEQUENCE: 3
agtccgtggt agggcaggtt ggggtgact                                     29

<210> SEQ ID NO 4
<211> LENGTH: 15
<212> TYPE: RNA
<213> ORGANISM: ARTIFICIAL
<220> FEATURE:
<223> OTHER INFORMATION: thrombin binding oligonucleotide

<400> SEQUENCE: 4
gguuggugug guugg                                                    15

<210> SEQ ID NO 5
<211> LENGTH: 19
<212> TYPE: RNA
<213> ORGANISM: ARTIFICIAL
<220> FEATURE:
<223> OTHER INFORMATION: thrombin binding oligonucleotide

<400> SEQUENCE: 5
ggguugggug uggguuggg                                                19
```

```
<210> SEQ ID NO 6
<211> LENGTH: 29
<212> TYPE: RNA
<213> ORGANISM: ARTIFICIAL
<220> FEATURE:
<223> OTHER INFORMATION: thrombin binding oligonucleotide

<400> SEQUENCE: 6
aguccguggu agggcagguu ggggugacu                                         29

<210> SEQ ID NO 7
<211> LENGTH: 15
<212> TYPE: DNA
<213> ORGANISM: ARTIFICIAL
<220> FEATURE:
<223> OTHER INFORMATION: antisense oligonucleotide

<400> SEQUENCE: 7
ccaaccacac caacc                                                        15

<210> SEQ ID NO 8
<211> LENGTH: 19
<212> TYPE: DNA
<213> ORGANISM: ARTIFICIAL
<220> FEATURE:
<223> OTHER INFORMATION: antisense oligonucleotide

<400> SEQUENCE: 8
cccaacccac acccaaccc                                                    19

<210> SEQ ID NO 9
<211> LENGTH: 29
<212> TYPE: DNA
<213> ORGANISM: ARTIFICIAL
<220> FEATURE:
<223> OTHER INFORMATION: antisense oligonucleotide

<400> SEQUENCE: 9
agtcacccca acctgcccta ccacggact                                         29

<210> SEQ ID NO 10
<211> LENGTH: 15
<212> TYPE: RNA
<213> ORGANISM: ARTIFICIAL
<220> FEATURE:
<223> OTHER INFORMATION: antisense oligonucleotide

<400> SEQUENCE: 10
ccaaccacac caacc                                                        15

<210> SEQ ID NO 11
<211> LENGTH: 19
<212> TYPE: RNA
<213> ORGANISM: ARTIFICIAL
<220> FEATURE:
<223> OTHER INFORMATION: antisense oligonucleotide

<400> SEQUENCE: 11
cccaacccac acccaaccc                                                    19

<210> SEQ ID NO 12
<211> LENGTH: 29
<212> TYPE: RNA
<213> ORGANISM: ARTIFICIAL
<220> FEATURE:
<223> OTHER INFORMATION: antisense oligonucleotide
```

```
<400> SEQUENCE: 12
agucacccca accugcccua ccacggacu                                29
```